US011124775B2

(12) United States Patent
Bouille et al.

(10) Patent No.: US 11,124,775 B2
(45) Date of Patent: *Sep. 21, 2021

(54) RETROVIRAL PARTICLE COMPRISING AT LEAST TWO ENCAPSIDATED NONVIRAL RNAS

(71) Applicant: FLASH THERAPEUTICS, Toulouse (FR)

(72) Inventors: Pascale Bouille, Vincennes (FR); Jean-Christophe Pages, Paris (FR); Régis Gayon, Ramonville Saint-Agne (FR)

(73) Assignee: FLASH THERAPEUTICS, Toulouse (FR)

( * ) Notice: Subject to any disclaimer, the term of this patent is extended or adjusted under 35 U.S.C. 154(b) by 606 days.

This patent is subject to a terminal disclaimer.

(21) Appl. No.: 15/574,337

(22) PCT Filed: May 13, 2016

(86) PCT No.: PCT/FR2016/051152
§ 371 (c)(1),
(2) Date: Nov. 15, 2017

(87) PCT Pub. No.: WO2016/185125
PCT Pub. Date: Nov. 24, 2016

(65) Prior Publication Data
US 2018/0135025 A1    May 17, 2018

(30) Foreign Application Priority Data

May 15, 2015  (FR) ........................................ 1554381
Apr. 13, 2016  (FR) ........................................ 1653280

(51) Int. Cl.
| | |
|---|---|
| *C12N 15/867* | (2006.01) |
| *A61K 48/00* | (2006.01) |
| *C12N 15/11* | (2006.01) |
| *C07K 14/005* | (2006.01) |
| *C12N 7/01* | (2006.01) |
| *C12N 15/48* | (2006.01) |
| *C12N 15/49* | (2006.01) |
| *C12N 15/62* | (2006.01) |
| *C12N 7/00* | (2006.01) |
| *C12N 7/02* | (2006.01) |
| *C12N 15/86* | (2006.01) |
| *C12N 7/04* | (2006.01) |

(52) U.S. Cl.
CPC ............ *C12N 7/00* (2013.01); *A61K 48/0008* (2013.01); *C07K 14/005* (2013.01); *C12N 7/025* (2013.01); *C12N 7/045* (2013.01); *C12N 15/86* (2013.01); *A61K 48/00* (2013.01); *C07K 2319/85* (2013.01); *C12N 2740/15021* (2013.01); *C12N 2740/16042* (2013.01); *C12N 2740/16051* (2013.01); *C12N 2740/16052* (2013.01); *C12N 2740/16071* (2013.01); *C12N 2740/16222* (2013.01); *C12N 2795/18152* (2013.01)

(58) Field of Classification Search
None
See application file for complete search history.

(56) References Cited

U.S. PATENT DOCUMENTS

2009/0075370 A1* 3/2009 Wilkes .................... C12N 15/86
                                                           435/320.1
2017/0145427 A1* 5/2017 Johnson .................... C12N 7/00

FOREIGN PATENT DOCUMENTS

| WO | 2007038757 A2 | 4/2007 |
| WO | 2007072056 A2 | 6/2007 |
| WO | 2013/014537   | 1/2013 |
| WO | 2013148302 A2 | 10/2013 |

OTHER PUBLICATIONS

Urbaneketal, RNA imaging in living cells—methods and applications, RNA Biology, 2014, pp. 1083-1095.*
Chen et al, HIV-1 RNA genome dimerizes on the plasma membrane in the presence of Gag protein, PNAS, 2015, E201-E208.*
Chamanian et al, A cis-acting element in retroviral genomic RNA links Gag-Pol ribosomal frameshifting to selective viral RNA encapsidation Cell Host Microbe. Feb. 13, 2013; 13(2): 181-192.*
Addgene, Lentiviral Guide, downloaded May 20, 2019, pp. 1-5.*
O'Keefe (Labome), Nucleic Acid Delivery: Lentiviral and Retroviral Vectors, Mater Methods 2013, pp. 1-21.*
Yi et al, Current Advances in Retroviral Gene Therapy, Current Gene Therapy, 2011, 11,218-228.*
Kotterman et al, Viral Vectors for Gene Therapy: Translational and Clinical OutlookAnnu. Rev. Biomed. Eng. 2015. 17:63-89.*

(Continued)

*Primary Examiner* — Maria Marvich
(74) *Attorney, Agent, or Firm* — Browdy and Neimark, PLLC

(57) ABSTRACT

The present invention relates to a retroviral system for the transfer of non-viral RNA into target cells and more particularly a retroviral particle capable of delivering multiple RNAs. More particularly, it relates to retroviral particles comprising a protein derived from the Gag polyprotein an envelope protein, optionally an integrase and at least two encapsidated non-viral RNAs, the encapsidated non-viral RNAs each comprising an RNA sequence of interest linked to an encapsidation sequence, each encapsidation sequence being recognised by a binding domain introduced into the protein derived from the Gag polyprotein and/or into the integrase.

6 Claims, 24 Drawing Sheets

Specification includes a Sequence Listing.

(56) References Cited

OTHER PUBLICATIONS

Mali, S, Delivery systems for gene therapy, Indian Journal of Human Genetics • Mar. 2013, pp. 1-8.*

M. Mark-Danieli et al., "Single Point Mutations in the Zinc Finger Motifs of the Human Immunodeficiency Virus Type 1 Nucleocapsid Alter RNA Binding Specificities of the Gag Protein and Enhance Packaging and Infectivity", Journal of Virology, pp. 7756-7767, vol. 79, No. 12 (Jun. 2005).

Tolga Sutlu et al.,"Inhibition of Intracellular Antiviral Oefense Mechanisms Augments Lentiviral Transduction of Human Natural Killer Cells: Implications for Gene Therapy", Human Gene Therapy, pp. 1090-1100, vol. 23, No. 10 (Oct. 2012).

Anne Prel et al.,"Highly efficient in vitro and in vivo delivery of functional RNAs using new versatile MS2-chimeric-retrovirus-like particles", Molecular Therapy-Methoos & Clinical Development, pp. 15039, vol. 2 (Oct. 2015).

Apolonia et al. Stable Gene Transfer to Muscle Using Nonintegrating Lentiviral Vectors Molecular Therapy Nov. 2007, vol. 15, No. 11, pp. 1947-1954 doi: 10.1038/sj.mt.6300281.

Caval, "Diverting the assembly properties of heterologous virus to study the life cyle of Hepatitis C", Mar. 2, 2012, pp. 1-190, abstract in English only.

Petit et al. Oligomerization within virions and subcellular localization of human immunodeficiency virus type 1 integrase. J. Virol, Jun. 1999; 73:5079-5088.

Nightingale et al. Transient Gene Expression by Nonintegrating Lentiviral Vectors Molecular Therapy, Jun. 2006 vol. 13, No. 6, doi:10.1016/j.ymthe.2006.01.008.

Chao et al. Structural basis for the coevolution of a viral RNA-protein complex. Nat Struct Mol Biol. Jan. 2008; 15(1):103-105. doi:10.1038/nsmb1327.

\* cited by examiner

Linear pCDNA.CMVLC. MS2 12X

Linear pCDNA.EF1.Fluorescent gene. MS2 12X

Linear pCDNA.EF1.CRE. MS2 12X

Linear pCDNA.EF1. PP7 12X

Linear P8.74- POL-PP7 Coat

RETROVIRAL PARTICLE COMPRISING AT LEAST TWO ENCAPSIDATED NONVIRAL RNAS

The Sequence Listing in ASCII text file format of 1,358 bytes in size, created on Nov. 8, 2017, with the file name "2017-11-15SequenceListing-BOUILLE2," filed in the U.S. Patent and Trademark Office on Nov. 15, 2017, is hereby incorporated herein by reference.

BACKGROUND OF THE INVENTION

Field of the Invention

The present invention concerns a retroviral system for transferring non-viral RNA into target cells and more particularly concerns a retroviral particle capable of delivering multiple RNAs. The invention also concerns compositions comprising these retroviral particles, kits for production thereof, manufacturing processes relating thereto, as well as the uses of the particles and the compositions.

Description of the Related Art

Introducing multiple RNAs into a target cell is a major stake in both research and development as in gene therapy.

The use of vectors derived from viruses has become a crucial method for gene transfer. Viral vectors today fall into two main categories:
- integrating vectors, which integrate themselves into the recipient genome, and
- non-integrating vectors, which usually form an extra chromosomal genetic element.

Integrating vectors such as gamma-retroviral vectors (RV) and lentiviral vectors (LV) are stably integrated. Non-integrating vectors, such as adenoviral (ADV) vectors and adeno-associated virus (AAV) vectors are quickly eliminated from cells which divide rapidly. Some factors influencing the choice of a particular vector, include its encapsidation capacity, its host or target cell range, its gene expression profile, its transduction efficiency and its capacity to elicit an immune response, which is particularly problematic if repeated transductions are required.

Certain applications require the use of non-integrating vectors such as in gene therapy or in numerous in vitro, ex vivo and in vivo applications. By way of example, the following may be cited:
- inducing the reprogramming of specialized cells into pluripotent cells, as well as inducing the differentiation of stem cells or pluripotent cells into specialized cells,
- the expression of antigens or proteins (whether or not toxic) simultaneously in a target cell,
- the expression of genetic engineering systems for example such as the CRE or TALEN protein or the CRISPR system, or any other system requiring protein or RNA expression.

One means for introducing RNAs into a target cell employs viral vectors based on viruses belonging to the Retroviridae family (also designated by the name Retrovirus family or RNA virus. As a matter of fact, during its replication cycle, a virus of the Retroviridae family possesses the capacity to convert its genome, constituted by RNA, into double-stranded DNA which will be integrated into the genome of the target cell. Particular examples of this Retrovirus family are gamma-retroviruses and lentiviruses.

The replication cycle of a retrovirus comprises a first phase of recognizing the target cell (or host) via binding to a membrane receptor. This recognition phase leads to the entry of the retrovirus into the host cell, after fusion with the membrane. The retroviral RNA is then copied into double-stranded DNA by reverse transcriptase, coded by the retrovirus, then integrated into the genome of the host cell. This viral genome is then transcribed by the host cell like all the other genes of the cell. This genome codes for all the proteins and sequences enabling the production of other viruses.

More particularly, three genes are common to all retroviruses: gag, pol and env.

Gag is a gene coding for a polyprotein, the proteins deriving from this polyprotein by cleavage, being structural proteins involved in the assembly of the viruses on replication. These structural proteins are more specifically the matrix protein (MA), the capsid protein (CA) and the nucleocapsid protein (NC).

Pol is a gene coding for the integrase, reverse transcriptase and protease enzymes.

Env is a gene coding for envelope glycoproteins.

These three genes thus make it possible to copy the retroviral RNA into double-stranded DNA, integrate that DNA into the genome of the host cell then generate the structure of newly synthesized retroviruses: envelope, capsid and nucleocapsid proteins. However, in order for the newly synthesized retrovirus to be complete, it is necessary to encapsidate two copies of the retroviral RNA within each of these structures. This encapsidation of two copies of the retroviral RNA into the structure is carried out by the recognition by the nucleocapsid protein of an encapsidation sequence called Psi (for "Packaging Signal") carried by the copy of the retroviral RNA.

When a viral vector derived from a retrovirus is used for the purposes of gene therapy, at least part of the regions coding for gag, pol and/or env is dissociated between the encapsidation system and the system for expressing the sequence of interest. The sequences coding for gag and pol, for example, are carried by the encapsidation plasmid providing in trans the proteins that are necessary for producing the viral vectors. The encapsidation sequence like the sequence of interest is carried by independent systems, in order to make the retrovirus non-replicating.

However, in certain cases, the random integration of the RNA sequence of interest into the genome of the host cell can interrupt an open reading phase and block the expression of important genes. Furthermore, for some applications, such as the reprogramming of cells or the differentiation of stem cells, it is recommended that the transient expression of a sequence of interest be carried out transiently.

The application WO2007/072056 describes a viral vector system comprising env, gag, optionally gag/pol as well as an RNA sequence containing a heterologous encapsidation signal which is recognized by a corresponding RNA binding domain associated with gag or with gag/pol. This system is described in the application as being non-integrating and enabling transient expression.

However, the efficiency of such systems remains limited. In particular, in order for a target cell to express an RNA of interest transferred by these systems, it is generally necessary to introduce into the cell several copies of that RNA of interest and therefore to use high MOI (standing for "multiplicity of infection"). The MOI corresponds to the ratio of the number of introduced vector systems to the number of cells to infect. A high MOI indeed makes it possible to introduce several copies of the RNA of interest into the cells by enabling a same cell to undergo several infections. However, although it may enable the level of expression of the transferred RNA of interest, the use of high MOI also leads to a degree of toxicity, on account of the multiple infections suffered by the cell.

There is therefore still a need for viral vector systems that are more efficient and less toxic.

SUMMARY OF THE INVENTION

The work of the inventors has enabled a vector system to be produced that is capable of delivering several RNAs of interest into a same cell in a single infection.

The present invention thus relates to a retroviral particle comprising a protein coming from the Gag polyprotein, an envelope protein, optionally an integrase and at least two encapsidated non-viral RNAs, the encapsidated non-viral RNAs each comprising an RNA sequence of interest linked to an encapsidation sequence, each encapsidation sequence being recognized by a binding domain introduced into the protein coming from the Gag polyprotein and/or into the integrase.

The retroviral particle according to the invention makes it possible to introduce at least two non-viral RNAs, preferably 3, into a cell by a single infection. The introduction of such particles into the cells may be carried out by method that is in vivo, in vitro or ex vivo.

DETAILED DESCRIPTION OF THE INVENTION

By "protein coming from the Gag polyprotein", is meant any protein resulting from the cleavage of the Gag polyprotein. More particularly, it is a nucleocapsid protein, a matrix protein (for example, in retroviral particles derived from the MoMuLV type murine virus) or the p12 protein, specific to gamma-retroviruses.

By "envelope protein" is meant any envelope protein, including a pseudotyping envelope protein. By way of example, it is possible to cite the Ampho envelope protein, the ecotropic envelope protein, the envelope protein of the Moloney murine leukemia virus (MoMuLV), the envelope protein of the Feline Immunodeficiency virus (FIV), the envelope protein of the Harvey murine sarcoma virus (HaMuSV), the envelope protein of the murine mammary tumor virus (MuMTV), the envelope protein of the Rous Sarcoma virus (RSV), the envelope protein of the measles virus (MV), the envelope protein of the Gibbon leukemia virus (GalV), the protein of the feline endogonous virus (RD114) or the envelope protein of the vesicular stomatitis virus (VSV-G). More particularly the envelope protein is the Ampho envelope protein, the ecotropic envelope protein, the envelope protein of the Moloney murine leukemia virus (MoMuLV), the envelope protein of the Feline Immunodeficiency virus (FIV), the envelope protein of the Harvey murine sarcoma virus (HaMuSV), the envelope protein of the murine mammary tumor virus (MuMTV), the envelope protein of the Rous Sarcoma virus (RSV), the envelope protein of the measles virus (MV), the envelope protein of the Gibbon leukemia virus (GalV) or the envelope protein of the vesicular stomatitis virus (VSV-G). The envelope protein may thus be modified to target certain cell types or certain applications (the use of surface receptors as envelope protein).

It is also possible to modify the envelope protein with an antibody, a glycolipid and/or a particular ligand in order to target a particular receptor and/or cell type.

Preferably, the envelope protein is the VSV-G protein.

By "integrase" is meant the enzyme protein coded by the pol gene, which enables the integration of the retroviral DNA into the DNA of the infected cell by the retrovirus on replication of said retrovirus.

By "encapsidation sequence" is designated an RNA motif (three-dimensional structure and sequence) specifically recognized by a binding domain. Preferably, the encapsidation sequence is a stem-loop motif. Still more preferably, the encapsidation sequence of the retroviral particle is the RNA stem-loop motif of the bacteriophage MS2 or of the phage PP7 for example such as that resulting from the sequence ctagaaaacatgaggatcacccatgtctgcag (SEQ ID No. 1) or (ctagaaggagcagacgatatggcgtcgctccctgcag SEQ ID No. 5) respectively. The stem-loop motif and more particularly the RNA stem-loop motif of the bacteriophage MS2 or that of the RNA of the phage PP7, may be used alone or repeated several times, preferably from 2 to 25 times, more preferably from 2 to 18 times, for example from 6 to 18 times.

By "binding domain" is meant the whole or part of a protein specifically binding to the encapsidation sequence linked to the RNA sequence of interest. More particularly, it is a protein, whether or not mutant, defined by a three-dimensional structure, specifically binding to the encapsidation sequence. Preferably, the binding domain is a heterologous domain. More preferably, the binding domain is the Coat protein of the bacteriophage MS2, of the phage PP7 or of the Qβ phage, the nun protein of the HK022 prophage, the U1A protein or the hPum protein.

More preferably, the binding domain is the Coat protein of the bacteriophage MS2 or of the phage PP7.

Still more preferably, when the binding domain is the Coat protein of the phage PP7, the sequence thereof is deficient for self-assembly, by virtue of a deletion of the amino acids 67 to 75 (PCPΔFG) (Chao et al. 2008). Preferably, the Coat protein sequence of the phage PP7 is codon-optimized for human cells, that is to say that the bases of the DNA are chosen to code for amino adds preferably present in the human species.

By "each sequence" it is meant that the encapsidation sequences may be identical or different, depending on whether those encapsidation sequences are recognized by an identical or different binding domain. Indeed, the retroviral particle according to the invention may comprise one or several binding domains. When several binding domains are introduced, these may be in the Gag polyprotein and/or in the integrase.

The binding domain enables not only the recognition of the encapsidation sequence but also the encapsidation of the RNAs bearing the encapsidation sequence in the particle (or in the present case, of a non-viral RNA linked to an encapsidation sequence).

By "encapsidation" is meant the packaging of an RNA in the viral capsid of a viral particle. It will be noted that in the present invention, the encapsidation of the non-viral RNAs is made by recognition of a non-viral encapsidation signal, in particular other than Psi.

"Sequence of Interest" refers to a sequence coding for a function presenting an interest for the user. More particularly, the sequence of interest carried by each of the two encapsidated non-viral RNAs may be identical or different.

Using the particles according to the invention, it is possible to transfer identical or different non-viral RNAs into target cells.

As the encapsidated RNAs are non-viral, these RNAs do not present sites that recognize the proteins coded by the pol gene.

This is because these non-viral RNAs do not participate in the early steps of the replication cycle of the retroviruses, i.e.:

The copying of the single-stranded viral RNA into double-stranded DNA by reverse transcriptase;

The maturation of the double-stranded DNA by recognition of the LTR ends by the integrase and maturation of the cytoplasm pre-integration complex into nuclear pre-integration complex.

These viral proteins (inverse transcriptase, integrase) coded by the pol gene are thus optional in the particle and the pol gene can thus either be present, or be deleted partially or totally. Preferably, the pol gene is either present, or is partially deleted.

It will be noted that the retroviral particles according to the invention comprise genetic material that is both viral and non-viral:

the gag gene, which may be viral or chimeric. More particularly, the gag gene is chimeric when the binding domain or domains is or are introduced therein.

Optionally, the pol gene, which may be viral or chimeric. As the pol gene codes for several enzymes, the sequences relating to those enzymes may be deleted totally or partially, be present and non-functional, or be present and functional. More particularly, the pol gene is chimeric when the binding domain or domains is or are introduced into the integrase.

At least two non-viral RNAs, each non-viral RNA being a carrier of a sequence of interest and of an encapsidation sequence. More particularly, these non-viral RNAs are free of any viral sequence.

More specifically, the retroviral particles according to the invention make it possible to introduce, into target cells, RNAs capable of inducing:

The transfer of one or more coding sequences of interest that are endogenous or exogenous to the target cell.

The transfer of one or more non-coding RNAs such as RNAs capable of inducing an effect on gene expression, for example via shRNA, miRNA, sgRNA, LncRNA or circRNA.

The transfer of cell RNAs, of messanger RNA type or other type (miRNA, etc.), sub genome replicons of virus RNA (VHC, etc.) or complete virus RNA genomes.

The simultaneous expression of coding or non-coding sequences that are endogenous or exogenous to the target cell, The participation in the genome modification of the target cell by genetic engineering systems, for example the CRISPR system.

Advantageously, the retroviral particle according to the invention comprises a nucleocapsid protein, an envelope protein, optionally an integrase and at least two encapsidated non-viral RNAs, the encapsidated non-viral RNAs each comprising an RNA sequence of interest linked to an encapsidation sequence, each encapsidation sequence being recognized by a binding domain introduced into the nucleocapsid protein and/or into the integrase.

By "nucleocapsid protein" is meant the structural protein NC coded by the gag gene. When the binding domain is introduced into the nucleocapsid protein, that protein is then a chimeric protein, coming from a chimeric gag gene.

When the binding domain is introduced into the integrase, the integrase is then a chimeric protein, coming from a chimeric pol gene.

By "chimeric protein" is designated a recombinant protein comprising several different protein sequences that are combined.

According to a first embodiment, in the retroviral particle according to the invention, the binding domain is introduced into the nucleocapsid protein and the at least two non-viral encapsidated RNAs are distinguished by their RNA sequence.

This first embodiment enables early transient expression of the RNAs of interest, without any associated integration event in the genome of the target cells.

As a matter of fact, on placing a particle according to this first embodiment in contact with a target cell, the membrane of the retroviral particle and that of the target cell will combine and enable the release of the content of the particle into the target cell. The RNAs are then released into the cytoplasm and the cell mechanisms enable those RNAs to be directly translated into protein(s), that is to say without additional steps such as reverse transcription, translocation into the nucleus or integration into the genome of the target cell.

More particularly, the at least two non-viral RNAs have the same encapsidation sequence. In this case, the at least two non-viral encapsidated RNAs are distinguished from each other by their RNA sequence of interest, that is to say that the RNA sequences of interest comprised in the two non-viral encapsidated RNAs are different. "Different" refers to sequences of interest that are not identical or have a difference not resulting from a spontaneous mutation or a mutation unintentionally chosen by the manipulator.

Alternatively, the at least two non-viral RNAs have two different encapsidation sequences. These at least two encapsidation sequences are then recognized by at least two different binding domains, at least one of these domains being introduced into the nucleocapsid protein. In this case, the at least two non-viral encapsidated RNAs may comprise identical or different sequences of interest.

It is possible to encapsidate at least two non-viral RNAs, preferably three non-viral RNAs.

According to a particular embodiment of the first embodiment, a second binding domain is introduced into the nucleocapsid protein of the retroviral particle according to the invention.

By way of example, the second binding domain may be the Coat protein of the bacteriophage MS2 when the first binding domain is the Coat protein of the phage PP7 or the second binding domain may be the Coat protein of the phage PP7 when the first binding domain is the Coat protein of the bacteriophage MS2.

In this case, at least two non-viral encapsidated RNAs bear different encapsidation sequences, each encapsidation sequence respectively corresponding to the first and second binding domain introduced into the nucleocapsid protein.

More particularly, when three non-viral RNAs are encapsidated:

at least two of the encapsidated non-viral RNAs present the same encapsidation sequence corresponding to the first binding domain and are distinguished from each other solely by their RNA sequence of interest, the third encapsidated non-viral RNA may bear an identical or different encapsidation sequence. When the encapsidation sequence is different, this may correspond to a second binding domain introduced into the nucleocapsid protein.

Other binding domains may also be introduced into the nucleocapsid protein.

In addition to the binding domain or domains introduced into the nucleocapsid protein, it is also possible to introduce a binding domain into the integrase.

The Integrase is then a chimeric protein, coming from a chimeric pol gene.

Preferably, when the binding domain is introduced into the integrase, the integrase sequence is mutated at the C-terminal domain in order to insert the binding domain sequence. Still more preferably, the integrase sequence is mutated at the C-terminal domain so as to introduce that of the Coat protein of the bacteriophage MS2 or of the phage PP7.

In this case, the at least two non-viral encapsidated RNAs may bear different encapsidation sequences, each encapsidation sequence corresponding to the binding domains introduced into the nucleocapsid protein and into the integrase respectively.

More particularly, when three non-viral RNAs are encapsidated:
at least two of the encapsidated non-viral RNAs present the same encapsidation sequence corresponding to the first binding domain and are distinguished from each other solely by their RNA sequence of interest,
the third encapsidated non-viral RNA bearing a different encapsidation sequence, corresponding to a second binding domain introduced into the integrase.

Other binding domains may also be introduced into the integrase.

Advantageously, the retroviral particle according to the invention is a lentiviral particle.

Preferably, in such a lentiviral particle:
the binding domain is the Coat protein of the bacteriophage MS2,
the encapsidation sequence of the non-viral RNAs is a stem-loop sequence of MS2,
the nucleocapsid protein is the nucleocapsid protein (NC) of HIV belonging to the chimeric Gag polyprotein, the NC sequence being mutated at the second zinc finger in order to insert the Coat protein sequence of the bacteriophage MS2.
Advantageously:
The envelope protein is the VSV-G protein coding for the envelope protein of the Vesicular stomatitis virus.
The encapsidation sequence comprises from 2 to 25 repetitions of the MS2 stem-loop sequence, preferably from 6 to 18 repetitions of the stem-loop sequence, still more preferably from 10 to 14, for example 12 repetitions. Preferably, the stem-loop sequence is the following: ctagaaaacatgaggatcacccatgtctgcag (SEQ ID No. °1).
Or, preferably, in such a lentiviral particle:
the binding domain is the Coat protein of the phage PP7,
the encapsidation sequence of the non-viral RNAs is a stem-loop sequence of PP7,
the nucleocapsid protein is the nucleocapsid protein (NC) of HIV belonging to the chimeric Gag polyprotein, the NC sequence being mutated at the second zinc finger in order to insert the Coat protein sequence of the PP7 bacteriophage.
Advantageously:
The envelope protein is the VSV-G protein coding for the envelope protein of the Vesicular stomatitis virus.
The encapsidation sequence comprises from 2 to 25 repetitions of the PP7 stem-loop sequence, preferably from 2 to 18 repetitions of the stem-loop sequence, still more preferably from 2 to 12, for example 6 repetitions. Preferably, the stem-loop sequence is the following: ctagaaggagcagacgatatggcgtcgctccctgcag (SEQ ID No. °5).

Optionally, the second binding domain introduced into the integrase may be the Coat protein of the phage PP7 if the first binding domain is the Coat protein of the bacteriophage MS2, or the second binding domain introduced into the integrase may be the Coat protein of the bacteriophage MS2 if the first binding domain is the Coat protein of the phage PP7.

According to a second embodiment, the invention concerns a retroviral particle comprising a protein coming from the Gag polyprotein, preferably a nucleocapsid protein, an envelope protein, an integrase and at least two non-viral encapsidated RNAs, the encapsidated non-viral RNAs each comprising an RNA sequence of interest linked to an encapsidation sequence, each encapsidation sequence being recognized by a binding domain introduced into the integrase and, optionally, by a binding domain introduced into a protein coming from the Gag polyprotein, preferably a nucleocapsid protein.

This second embodiment enables transient expression of the RNAs of interest, without any associated integration event in the genome of the target cells.

Preferably, in this second embodiment, the integrase sequence is mutated at the C-terminal domain in order to insert the binding domain sequence.

Advantageously, the binding domain is a heterologous domain. More particularly, the binding domain is the Coat protein of the bacteriophage MS2, of the phage PP7 or of the Qβ phage, the nun protein of the HK022 prophage, the U1A protein or the hPum protein.

Preferably, the integrase sequence is mutated at the C-terminal domain so as to introduce that of the Coat protein of the bacteriophage MS2 or of the phage PP7.

The at least two non-viral RNAs may or may not present the same encapsidation sequence.

Similarly, the at least two non-viral encapsidated RNAs may or may not present the same RNA sequence of interest.

Preferably, the at least two non-viral encapsidated RNAs are distinguished from each other by their RNA sequence of interest, that is to say that the RNA sequences of interest comprised in the two non-viral encapsidated RNAs are different.

More particularly; the at least two non-viral RNAs present the same encapsidation sequence, the latter being recognized by the binding domain introduced into the integrase.

It is possible to encapsidate at least two non-viral RNAs, preferably three non-viral RNAs.

According to a particular embodiment of the second embodiment, a second binding domain is introduced into the integrase of the retroviral particle according to the invention.

By way of example, the second binding domain may be the Coat protein of the bacteriophage MS2 when the first binding domain is the Coat protein of the phage PP7 or the second binding domain may be the Coat protein of the phage PP7 when the first binding domain is the Coat protein of the bacteriophage MS2.

In this case, at least two non-viral encapsidated RNAs bear different encapsidation sequences, each encapsidation sequence respectively corresponding to the first and second binding domain introduced into the integrase.

More particularly, when three non-viral RNAs are encapsidated:
at least two of the encapsidated non-viral RNAs present the same encapsidation sequence corresponding to the first binding domain, these two non-viral RNAs possibly being distinguishable from each other by their RNA sequence of interest, the third encapsidated non-viral RNA may bear an identical or different encapsidation sequence. When the encapsidation sequence is different, this may correspond to a second binding domain introduced into the integrase.

Other binding domains may also be introduced into the integrase.

In addition to the binding domain or domains introduced into the integrase, it is also possible to introduce a binding domain into the nucleocapsid protein.

The nucleocapsid protein is then a chimeric protein, coming from a chimeric gag gene.

In this case, the at least two non-viral encapsidated RNAs may bear different encapsidation sequences, each encapsidation sequence corresponding to the binding domains introduced into the integrase and into the nucleocapsid protein respectively.

More particularly, when three non-viral RNAs are encapsidated:

at least two of the encapsidated non-viral RNAs present the same encapsidation sequence corresponding to the first binding domain introduced into the integrase, these two non-viral RNAs possibly being distinguishable from each other by their RNA sequence of interest, the third encapsidated non-viral RNA bears a different encapsidation sequence, corresponding to a second binding domain introduced into the nucleocapsid protein.

Other binding domains may also be introduced into the nucleocapsid protein.

Advantageously, the retroviral particle according to the invention is a lentiviral particle.

When the retroviral particle is a lentiviral particle, it is possible to transiently express the RNAs of interest, without any associated integration event in the genome of the target cells, in particular quiescent cells.

As a matter of fact, apart from its role in the integration reaction itself, the integrase (IN) participates in different steps of the replication cycle of the retroviruses such as the morphogenesis of the viral particle, the reverse transcription and the nuclear import of the pre-integration complex (PIC).

More particularly, in lentiviruses, the integrase contains nuclear localization sequences (NLSs) enabling it to be located in the nucleus by virtue of the PIC. Therefore, when the encapsidation of the non-viral RNAs performed by a binding domain carried by an integrase of a lentivirus, the encapsidated non-viral RNAs will be transported into the nucleus of the target cell. As a matter of fact, on placing a lentiviral particle according to this second embodiment in contact with a target cell, the membrane of the particle and that of the target cell will combine and enable the release of the content of the capsid into the target cell. The RNAs are then taken charge of by the integrase which, via the PICs, will enable the import of the RNAs into the nucleus. This taking charge is particularly advantageous for certain applications, such as expression in quiescent cells. In the case of retroviral particles, other than lentiviruses, the integrase does not contain these NLSs and is therefore found to be located in the cytoplasm. It is however possible to add, into this type of integrase, NLS sequences in order to induce nuclear localization of the integrase and thus of the RNAs taken charge of by that integrase.

This taking charge is also particularly useful for a CRISPR system, which calls upon RNA guides which become hybridized specifically with the genome of the target cell. Once hybridized, these RNA guides guide an endonuclease (Cas9), which will enable the modification of a specific locus of the target cell genome.

More particularly, in such a lentiviral particle:
the binding domain is the Coat protein of the bacteriophage MS2,
the encapsidation sequence of the non-viral RNAs is a stem-loop sequence of MS2,
the integrase is a chimeric enzyme protein of which the sequence has mutated at the C-terminal domain in order to insert the Coat protein sequence of the bacteriophage MS2.

Or, more particularly, in such a lentiviral particle:
the binding domain is the Coat protein of the phage PP7,
the encapsidation sequence of the non-viral RNAs is a stem-loop sequence of PP7,
the integrase is a chimeric enzyme protein of which the sequence has mutated at the C-terminal domain in order to insert the Coat protein sequence of the phage PP7.

Optionally, the second binding domain introduced into the nucleocapsid may be the Coat protein of the phage PP7 if the first binding domain is the Coat protein of the bacteriophage MS2 or the second binding domain introduced into the integrase may be the Coat protein of the bacteriophage MS2 If the first binding domain is the Coat protein of the phage PP7.

As a matter of fact, the integrase (IN) is composed of three distinct functional domains, each indispensable to ensure a complete integration reaction. The N-terminal domain contains a zinc finger type motif which stabilizes the folded structure of the IN and increases the catalytic activity of the enzyme. The central domain of the IN contains the DDE amino acid motif to which is attributed the catalytic activity of the enzyme. This control domain is also involved in the recognition of the nucleotide sequence conserved at each end of the retroviral DNA. The C-terminal domain is the least conserved in the retrovirus family. It possesses the activity of binding to the DNA and is indispensable for the maturation reactions of the 3' ends for strand transfer. Apart from its role in the integration reaction itself, IN participates in different steps of the replication cycle of the retroviruses such as the morphogenesis of the viral particle, the reverse transcription and the nuclear import of the pre-integration complex.

As described by Petit et al. (1999; J. Virol. P5079-5088), the insertion of an exogenous sequence in the C-terminal of the IN does not disturb the steps of production and transduction of target cells whereas a same insertion in the N-terminal does not enable detection of a transduction event.

The retroviral particle has thus been modified to contain the Coat protein of the bacteriophage MS2 in combination with the integrase protein (see FIG. I) or the Coat protein of the phage PP7 (see FIG. XXXVII). The p8.74 encapsidation plasmid, carrier of the pol gene coding for the integrase protein, is modified in order to insert the sequence coding the Coat protein in the C-terminal of the integrase by assembly PCR. The p8.74 plasmid is linearized by PCR then the Coat sequence, amplified in advance by PCR, is cloned at the C-terminal of the integrase, either directly end-to-end or with the addition of a linker.

Advantageously:
The envelope protein is the VSV-G protein coding for the envelope protein of the Vesicular stomatitis virus.
The encapsidation sequence comprises from 2 to 25 repetitions of the stem-loop sequence of MS2 and/or of PP7, according to the binding domain introduced, preferably from 2 to 18 repetitions, more preferably from 2 to 18 repetitions, such as from 6 to 18 repetitions of the stem-loop sequence, still more preferably for the stem-loop sequence of MS2, from 10 to 14, for example 12 repetitions.

Preferably, the stem-loop sequence is the following: ctagaaaacatgaggatcacccatgtctgcag (SEQ ID No. 1) when the binding domain is the Coat protein of MS2 and/or the stem-loop sequence is the following: ctagaaggagcagacgatatggcgtcgctccctgcag (SEQ ID No. 5) when the binding domain is the Coat protein of PP7.

Several examples of lentiviral particles according to the invention are described in more detail in the following examples:

- an MS2RLP or MS2 (NC)-RLP 12X particle is a lentiviral particle formed by encapsidation of RNAs bearing the stem-loop motif of the bacteriophage MS2, repeated 12 times, by the insertion of the Coat protein of the bacteriophage MS2 in the nucleocapsid,
- an MS2 (NC)-RLP 2X particle is a lentiviral particle formed by encapsidation of RNAs bearing the stem-loop motif of the bacteriophage MS2, repeated 2 times, by the insertion of the Coat protein of the bacteriophage MS2 in the nucleocapsid,
- an MS2 (NC)-RLP 6X particle is a lentiviral particle formed by encapsidation of RNAs bearing the stem-loop motif of the bacteriophage MS2, repeated 6 times, by the insertion of the Coat protein of the bacteriophage MS2 in the nucleocapsid,
- an MS2 (IN)-RLP 2X particle is a lentiviral particle formed by encapsidation of RNAs bearing the stem-loop motif of the bacteriophage MS2, repeated 2 times, by the insertion of the Coat protein of the bacteriophage MS2 In the integrase,
- an MS2 (IN)-RLP 6X particle is a lentiviral particle formed by encapsidation of RNAs bearing the stem-loop motif of the bacteriophage MS2, repeated 6 times, by the insertion of the Coat protein of the bacteriophage MS2 in the integrase,
- an MS2 (IN)-RLP 12X particle is a lentiviral particle formed by encapsidation of RNAs bearing the stem-loop motif of the bacteriophage MS2, repeated 12 times, by the insertion of the Coat protein of the bacteriophage MS2 in the integrase,
- a PP7 (NC)-RLP 2X particle is a lentiviral particle formed by encapsidation of RNAs bearing the stem-loop motif of the phage PP7, repeated 2 times, by the insertion of the Coat protein of the phage PP7 in the nucleocapsid,
- a PP7 (NC)-RLP 6X particle is a lentiviral particle formed by encapsidation of RNAs bearing the stem-loop motif of the phage PP7, repeated 6 times, by the insertion of the Coat protein of the phage PP7 in the nucleocapsid,
- a PP7RLP or PP7 (NC)-RLP 12X particle is a lentiviral particle formed by encapsidation of RNAs bearing the stem-loop motif of the phage PP7, repeated 12 times, by the insertion of the Coat protein of the phage PP7 in the nucleocapsid,
- a PP7 (IN)-RLP 2X particle is a lentiviral particle formed by encapsidation of RNAs bearing the stem-loop motif of the phage PP7, repeated 2 times, by the insertion of the Coat protein of the phage PP7 in the integrase,
- a PP7 (IN)-RLP 6X particle is a lentiviral particle formed by encapsidation of RNAs bearing the stem-loop motif of the phage PP7, repeated 6 times, by the insertion of the Coat protein of the phage PP7 in the integrase,
- a PP7 (IN)-RLP 12X particle is a lentiviral particle formed by encapsidation of RNAs bearing the stem-loop motif of the phage PP7, repeated 12 times, by the insertion of the Coat protein of the phage PP7 In the integrase.

Preferably, the lentiviral particle formed by encapsidation RNAs bears a stem-loop motif of the bacteriophage MS2 or of the PP7phage, repeated from 2 to 25 times, more preferably 2, 6 or 12 times.

Still more preferably, the particle according to the invention is chosen from MS2 (NC)-RLP 12X, PP7 (NC)-RLP 6X, PP7 (NC)-RLP 2X, MS2 (IN)-RLP 12X, PP7 (IN)-RLP 6X and PP7 (IN)-RLP 2X.

The Invention also concerns compositions comprising particles according to the invention.

More particularly, the compositions according to the invention are concentrated compositions. Advantageously, the compositions are also purified. These compositions may be concentrated and purified according to the method described in the application WO2013/014537.

Typically, the compositions according to the invention comprise less than 30% of DNA contaminants and less than 45% proteic contaminants relative to the crude supernatant. More particularly, the compositions according to the invention comprise less than 30% of DNA contaminants and less than 2% proteic contaminants relative to the crude supernatant.

"Crude supernatant" refers to the cell culture supernatant, comprising retroviral particles according to the invention, after clarifying. Such a clarifying step is more particularly described below in the methods of manufacturing particles according to the invention. When the harvesting of the supernatant is carried out several times, the crude supernatant then corresponds to all the supernatants harvested, combined (or "pooled") then clarified.

Optionally, the compositions according to the invention comprise less than 1% of DNA contaminants and less than 1% proteic contaminants relative to the crude supernatant.

The invention also relates to kits for production of particles according to the invention and to the methods for manufacturing those kits.

More particularly, the invention concerns a kit for producing particles according to the invention, comprising:

(i) an expression plasmid comprising at least one sequence of interest, for which upstream or downstream of that sequence is inserted an encapsidation sequence, (ii) an encapsidation plasmid coding for a protein coming from the Gag polyprotein and/or an integrase, which are chimeric, comprising a binding domain enabling an encapsidation sequence to be recognized, and (iii) an envelope plasmid coding for an envelope protein.

Such a kit may also comprise instructions for use of the plasmids contained in the kit.

More specifically, when the kit is directed to particles according to the first embodiment, this kit comprises:

(i) an expression plasmid comprising at least two different non-viral RNA sequences, each RNA sequence comprising a sequence of interest for which upstream or downstream of that sequence of interest is inserted an encapsidation sequence, or alternatively a first and a second expression plasmid each comprising a sequence of interest upstream or downstream of which is inserted an encapsidation sequence, (ii) an encapsidation plasmid coding for a chimeric nucleocapsid protein comprising a binding domain making it possible to recognize the encapsidation sequence, and, (iii) an envelope plasmid coding for an envelope protein.

The at least two non-viral RNA sequences are different because the sequences of interest are different and/or the encapsidation sequences are different.

Preferably, the kit producing particles according to the first embodiment comprises:

(i) an expression plasmid comprising at least two sequences of interest, for which upstream or downstream of each of these sequences is inserted an encapsidation sequence, or alternatively a first and a second expression plasmid each comprising a sequence of interest upstream or downstream of which is inserted an encapsidation sequence, the sequences of interest being different and the encapsidation sequences being identical, (ii) an encapsidation plasmid coding for a chimeric nucleocapsid protein comprising a binding domain making it possible to recognize the encapsidation sequence, and, (iii) an envelope plasmid coding for an envelope protein.

Advantageously; the kit produces lentiviral particles.

Preferably:

In the expression plasmid, the encapsidation sequence comprises from 2 to 25 repetitions of the MS2 stem-loop sequence, preferably from 6 to 18 repetitions of the stem-loop sequence, still more preferably from 10 to 14, for example 12 repetitions. Advantageously, the stem-loop sequence is the following: ctagaaaacatgaggatcaccatgtctgcag (SEQ ID NO:1).

In the encapsidation plasmid, the nucleocapsid protein is the nucleocapsid protein (NC) of HIV belonging to the Gag polyprotein, which NC is mutated at the second zinc finger in order to insert the Coat protein sequence of the bacteriophage MS2.

In the envelope plasmid, the envelope protein is the protein VSV-G coding for the envelope protein of the Vesicular stomatitis virus.

Or preferably:

In the expression plasmid, the encapsidation sequence comprises from 2 to 25 repetitions of the PP7 stem-loop sequence, preferably from 2 to 18 repetitions of the stem-loop sequence, still more preferably from 2 to 12, for example 6 repetitions. Advantageously, the stem-loop sequence is the following: ctagaaggagcagacgatatggcgtcgctccctgcag (SEQ ID No. 5).

In the encapsidation plasmid, the nucleocapsid protein is the nucleocapsid protein (NC) of HIV belonging to the Gag polyprotein, which NC is mutated at the second zinc finger in order to insert the Coat protein sequence of the phage PP7.

In the envelope plasmid, the envelope protein is the protein VSV-G coding for the envelope protein of the Vesicular stomatitis virus.

Optionally, the kit comprises a second encapsidation plasmid coding for a chimeric integrase comprising a binding domain making it possible to recognize an encapsidation sequence. The second binding domain may be identical to or different from the binding domain of the chimeric nucleocapsid protein.

By way of example of different binding domains:

the binding domain introduced into the nucleocapsid may be the Coat protein of MS2 and the binding domain introduced into the integrase may be the Coat protein of PP7, or the binding domain introduced into the nucleocapsid may be the Coat protein of PP7 and the binding domain introduced into the integrase may be the Coat protein of MS2.

Several binding domains may be introduced into each of the chimeric proteins.

Alternatively, when the kit is directed to particles according to the second embodiment, this kit comprises:

(i) an expression plasmid comprising at least one sequence of interest, for which upstream or downstream of that sequence is inserted an encapsidation sequence, (ii) an encapsidation plasmid coding for a chimeric integrase comprising a binding domain making it possible to recognize the encapsidation sequence, and, (iii) an envelope plasmid coding for an envelope protein.

Methods for manufacturing kits according to the invention are also provided. Typically, a method for manufacturing a kit according to the invention comprises:

(i) preparing an expression plasmid comprising at least one sequence of interest, for which upstream or downstream of that sequence is inserted an encapsidation sequence (ii) preparing an encapsidation plasmid coding for a protein coming from the Gag polyprotein and/or an integrase, which are chimeric, comprising a binding domain enabling an encapsidation sequence to be recognized, and (iii) preparing an envelope plasmid coding for an envelope protein.

More specifically, when the method concerns a kit which is directed to particles according to the first embodiment, it comprises:

(i) preparing an expression plasmid comprising at least two different non-viral RNA sequences, each RNA sequence comprising a sequence of interest for which upstream or downstream of that sequence of interest is inserted an encapsidation sequence, or alternatively a first and a second expression plasmid each comprising a sequence of interest upstream or downstream of which is inserted an encapsidation sequence, (ii) preparing an encapsidation plasmid coding for a chimeric nucleocapsid protein comprising a binding domain making it possible to recognize the encapsidation sequence, and, (iii) preparing an envelope plasmid coding for an envelope protein.

The at least two non-viral RNA sequences are different because the sequences of interest are different and/or the encapsidation sequences are different.

Preferably, this method comprises:

(I) preparing an expression plasmid comprising at least two sequences of interest, for which upstream or downstream of each of these sequences is inserted an encapsidation sequence, or alternatively a first and a second expression plasmid each comprising a sequence of interest upstream or downstream of which is inserted an encapsidation sequence, the sequences of interest being different and the encapsidation sequences being identical, (ii) preparing an encapsidation plasmid coding for a chimeric nucleocapsid protein comprising a binding domain making it possible to recognize the encapsidation sequence, and
(iii) preparing an envelope plasmid coding for an envelope protein.

Alternatively, when method concerns a kit which is directed to particles according to the second embodiment, this method comprises:
(i) preparing an expression plasmid comprising at least one sequence of interest, for which upstream or downstream of that sequence is inserted an encapsidation sequence,
(ii) preparing an encapsidation plasmid coding for a chimeric integrase comprising a binding domain making it possible to recognize the encapsidation sequence, and,
(iii) preparing an envelope plasmid coding for an envelope protein.

The invention also relates to methods for manufacturing particles according to the invention.

Such a method comprises a step of co-transfecting cells with:
(i) an expression plasmid comprising at least one sequence of interest, for which upstream or downstream of that sequence is inserted an encapsidation sequence,
(ii) an encapsidation plasmid coding for a protein coming from the Gag polyprotein and/or an integrase, which are chimeric, comprising a binding domain enabling an encapsidation sequence to be recognized, and
(iii) an envelope plasmid coding for an envelope protein.
and harvesting the supernatant of the transfected cells comprising the particles.

The cells employed in the methods of manufacturing particles according to the invention are producer cells, that is to say cells which, once transfected with the plasmids bearing the genetic material necessary to form retroviral particles, enable said particles to be formed. By way of example of producer cells, HEK293T may be cited.

By "co-transfecting step" is meant a transfecting step in which the transfection is carried out by placing producer cells in contact with the group of plasmids of the method of manufacturing the particles.

More specifically, when the manufacturing method is directed to producing particles according to the first embodiment, it comprises a step of co-transfecting cells with:
(i) an expression plasmid comprising at least two different non-viral RNA sequences, each RNA sequence comprising a sequence of interest for which upstream or downstream of that sequence of interest is inserted an encapsidation sequence, or alternatively a first and a second expression plasmid each comprising a sequence of interest upstream or downstream of which is inserted an encapsidation sequence,
(ii) an encapsidation plasmid coding for a chimeric nucleocapsid protein comprising a binding domain making it possible to recognize the encapsidation sequence, and,
(iii) an envelope plasmid coding for an envelope protein, and harvesting the supernatant of the transfected cells comprising the particles.

The at least two non-viral RNA sequences are different because the sequences of interest are different and/or the encapsidation sequences are different.

Preferably, this method of manufacturing particles comprises a step of co-transfecting cells with:

(i) an expression plasmid comprising at least two sequences of interest, for which upstream or downstream of each of these sequences is inserted an encapsidation sequence, or alternatively a first and a second expression plasmid each comprising a sequence of interest upstream or downstream of which is inserted an encapsidation sequence,
the sequences of interest being different and the encapsidation sequences being identical,
(ii) an encapsidation plasmid coding for a chimeric nucleocapsid protein comprising a binding domain making it possible to recognize the encapsidation sequence, and,
(iii) an envelope plasmid coding for an envelope protein, and harvesting the supernatant of the transfected cells comprising the particles.

Alternatively, when the manufacturing method is directed to producing particles according to the second embodiment, this method comprises a step of co-transfecting cells with:
(i) an expression plasmid comprising at least one sequence of interest, for which upstream or downstream of that sequence is inserted an encapsidation sequence,
(ii) an encapsidation plasmid coding for a chimeric integrase comprising a binding domain making it possible to recognize the encapsidation sequence, and,
(iii) an envelope plasmid coding for an envelope protein, and harvesting the supernatant of the transfected cells comprising the particles.

Preferably, all the methods for manufacturing particles according to the invention are carried out in accordance with the methods described in the application WO2013/014537.

More particularly, these methods for manufacturing particles are carried out on producer cells cultured in serum-free medium and no induction with sodium butyrate is carried out.

Advantageously, the supernatant is collected several times, for example between 3 and 6 times, at specific time intervals, such as time intervals of the order of the half-life of the retroviral particles. Typically, the harvesting of the supernatant is carried out 4 to 5 times, at intervals of time of the order of 6 to 18 h, preferably from 8 to 16 h, such as 8 h, 12 h and/or 16 h. Preferably, this harvesting is carried out after changing the culture medium of the cells, this change being carried out preferably at 24 h post-transfection.

The methods for manufacturing particles according to the invention also comprise a step in which the supernatant is clarified.

Preferably, the clarification of the supernatant is carried out by centrifuging.

Still more preferably, these methods of manufacturing particles according to the invention further comprise a step in which the supernatant is concentrated and/or purified.

Preferably, the concentration and purification is carried out by frontal ultrafiltration on centrifugation units.

Advantageously, the supernatant undergoes one or more additional steps of purification. These purification steps are preferably carried out by tangential ultrafiltration and/or by diafiltration. Still more preferably, the supernatant undergoes a step of tangential ultrafiltration followed by a step of diafiltration.

Tangential ultrafiltration is advantageously carried out with polysulfone hollow-fiber cartridges.

Optionally, the composition may then undergo a step of ion exchange chromatography, in particular anion exchange chromatography. The eluate produced in this chromatography step is then collected then concentrated again by frontal ultrafiltration on central centrifugation units. A composition resulting from such a method comprise less than 1% of DNA contaminants and less than 1% proteic contaminants relative to the crude supernatant.

The Invention also concerns compositions capable of being obtained by any one of the methods of manufacturing particles according to the invention.

Typically, these compositions comprise less than 30% of DNA contaminants and less than 45% proteic contaminants relative to the crude supernatant. More particularly, the compositions according to the invention comprise less than 30% of DNA contaminants and less than 2% proteic contaminants relative to the crude supernatant.

Optionally, the compositions according to the invention comprise less than 1% of DNA contaminants and less than 1% proteic contaminants relative to the crude supernatant.

Lastly, the invention concerns the use of a particle according to the invention, or of a composition according to the invention for transducing cells.

The use of the particles and compositions according to the invention is particularly advantageous for transducing primary cells and immortalized lines, in order to modify them transiently. The cells may be cells of mammals or other eukaryotes In particular, transduction of these cells may be made in vivo, in vitro or ex vivo.

BRIEF DESCRIPTION OF THE DRAWINGS

The invention will be better understood in the light of the following examples given by way of illustration, with reference to the drawings, which respectively represent.

FIG. 15 presents photographs of each animal at given times, FIGS. 16 and 17 being graphs representing the measurements of luciferase expression, at those times;

EXAMPLE 1: CONSTRUCTION OF MS2RLP LENTIVIRAL PARTICLES

Figure 1:
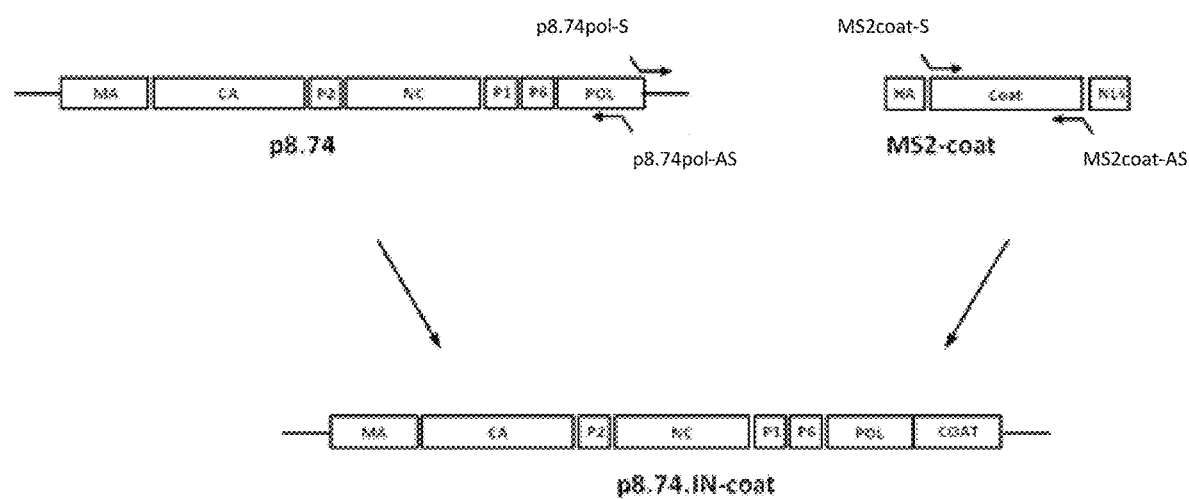
FIG. 1 is a diagram illustrating the modification of the lentiviral encapsidation plasmid p8.74 in order to insert a binding domain into the integrase sequence, this encapsidation plasmid being used for the production of lentiviral particles according to the invention.
Figure 2A:
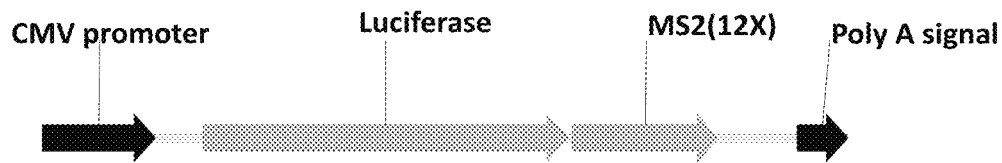
FIGS. 2A-2C present different diagrams for expression plasmid constructions bearing, as RNA sequence of interest, luciferase (FIG. 2A), a fluorescent reporter (FIG. 2B) or CRE (FIG. 2C), these expression plasmids being used for the production of MS2RLP lentiviral particles according to the invention.
Figure 2B:
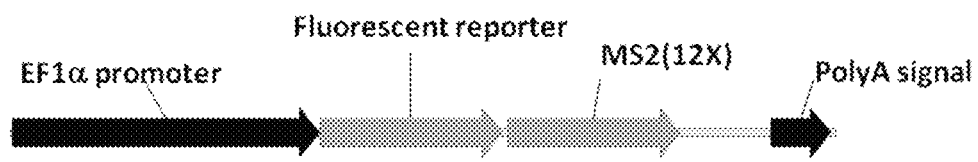
Figure 2C:
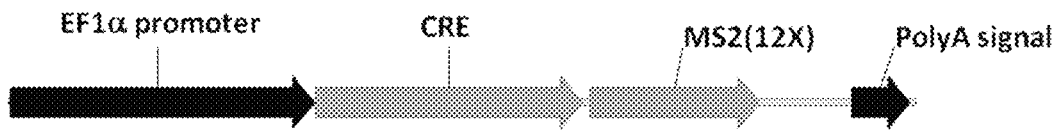
Figure 3A:
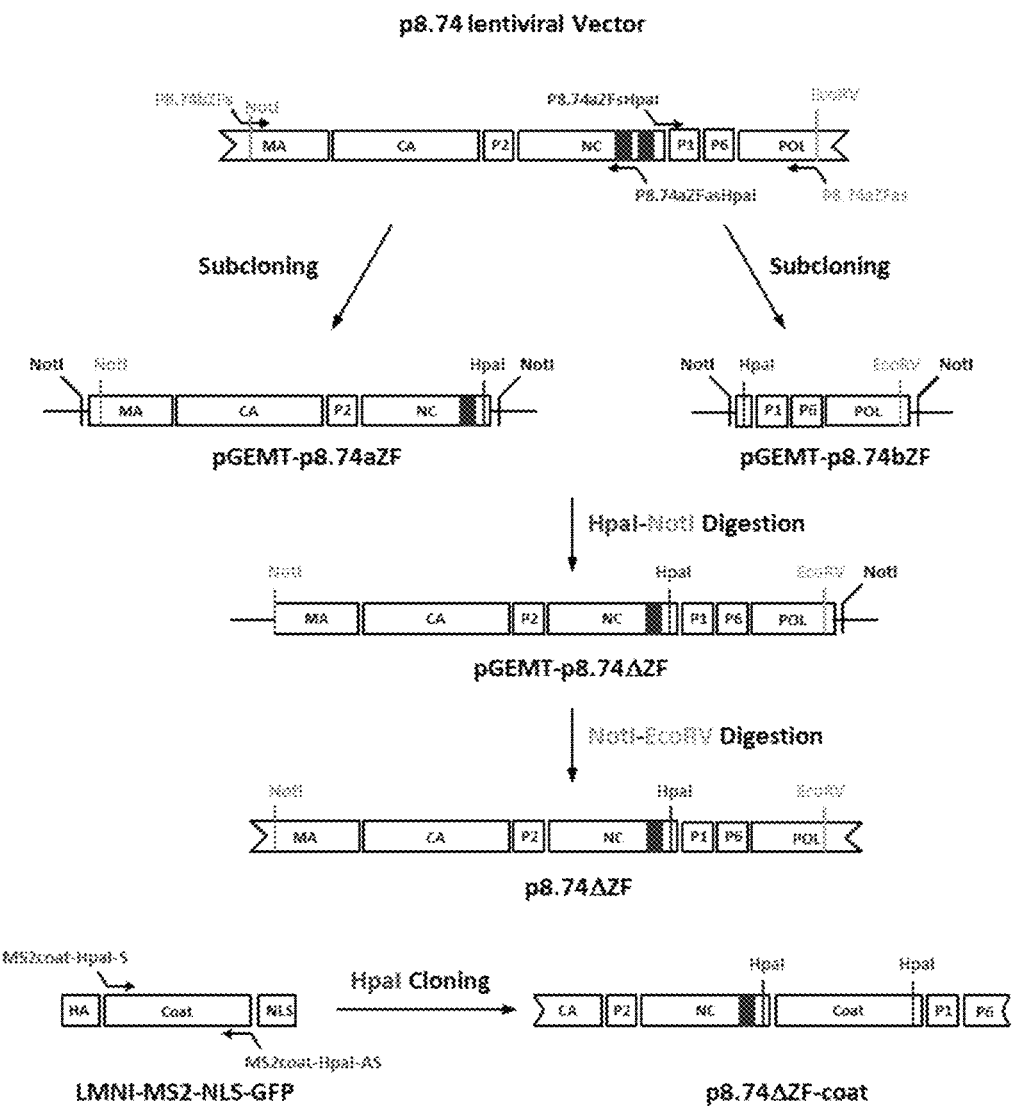
FIGS. 3A and 3B present diagrams illustrating the modification of the lentiviral encapsidation plasmid p8.74 In order to insert an MS2 Coat binding domain into the nucleocapsid sequence (FIG. 3A), and the plasmid construction resulting therefrom (FIG. 3B), this encapsidation plasmid being used for the production of MS2RLP lentiviral particles according to the invention.
Figure 3B:
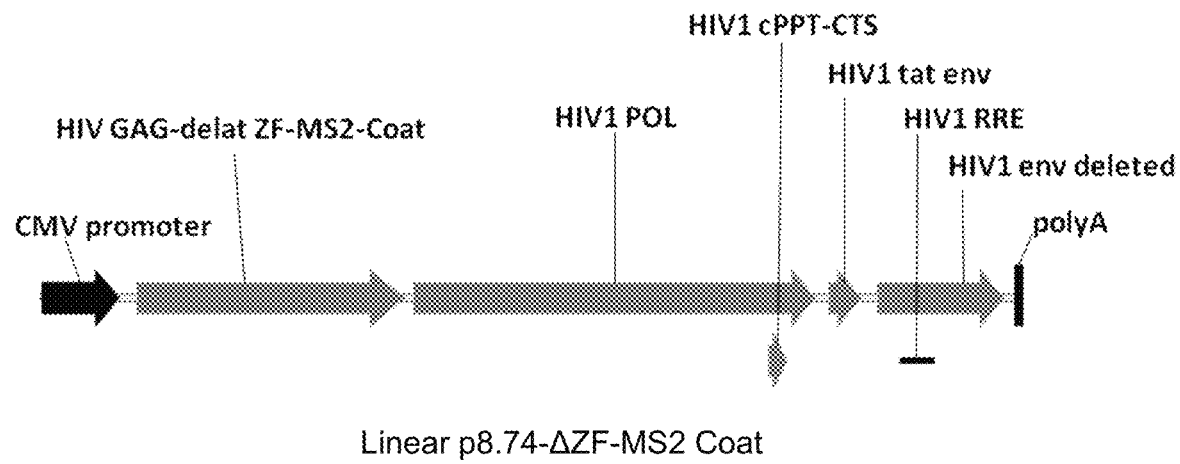
Figure 4:
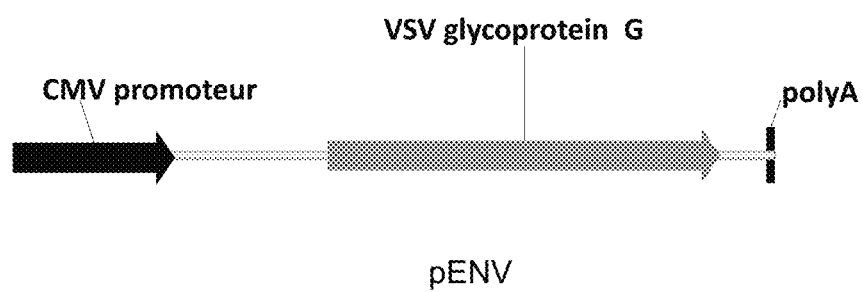
FIG. 4 is a diagram of envelope plasmid construction.
Figure 5A:
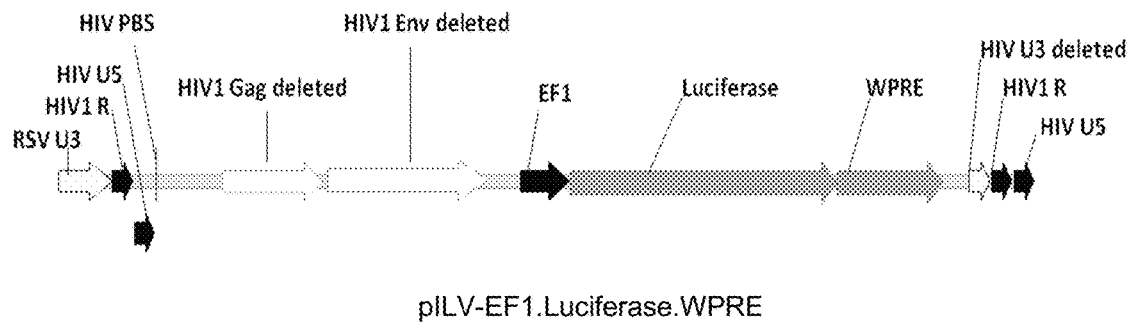
FIGS. 5A-5C present different diagrams of integrating lentiviral expression plasmid constructions bearing, as sequence of interest, luciferase (FIG. 5A), a fluorescent reporter (FIG. 5B) or CRE (FIG. 5C)
Figure 5B:
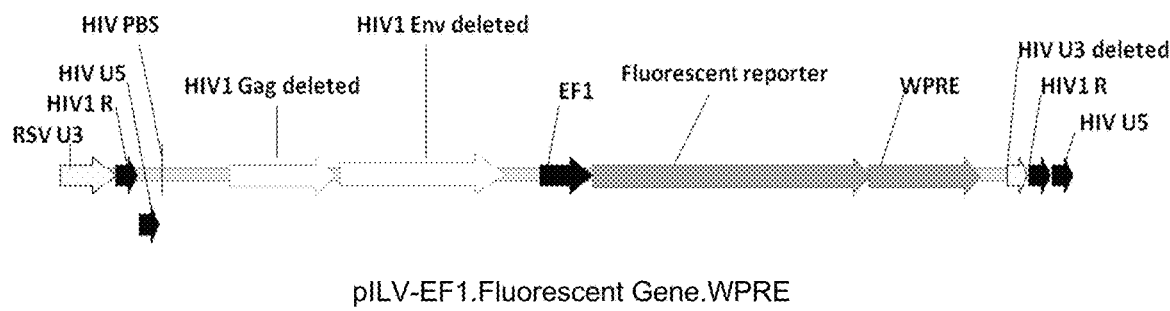
Figure 5C:
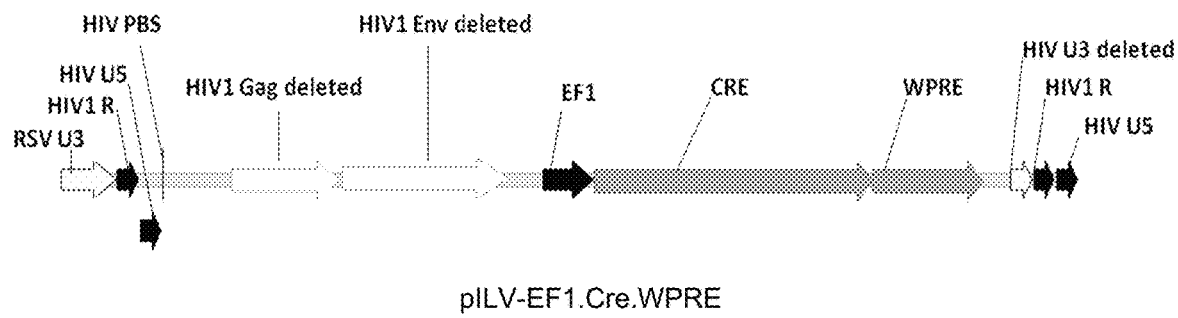
Figure 6:
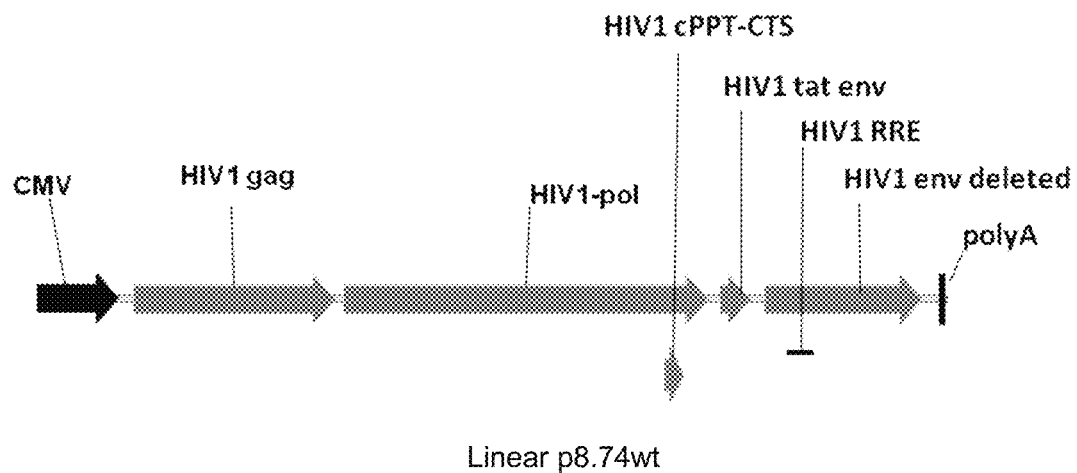
FIG. 6 is a diagram of construction of an encapsidation plasmid, this encapsidation plasmid being used for the production of integrating lentiviral vectors (ILVs)
Figure 7:
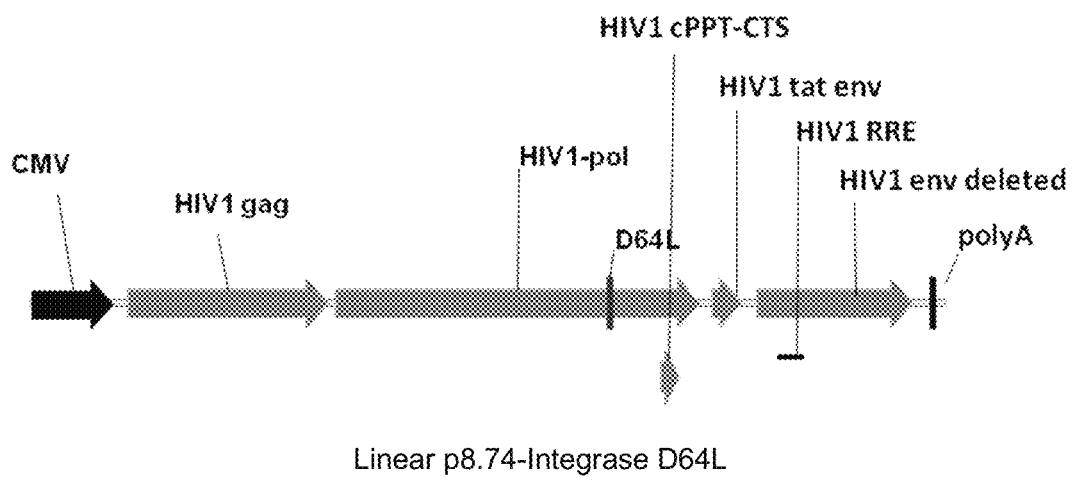
FIG. 7 is a diagram of construction of an encapsidation plasmid, this encapsidation plasmid being used for the production of integration-deficient lentiviral vectors (IDLVs)
Figure 8:
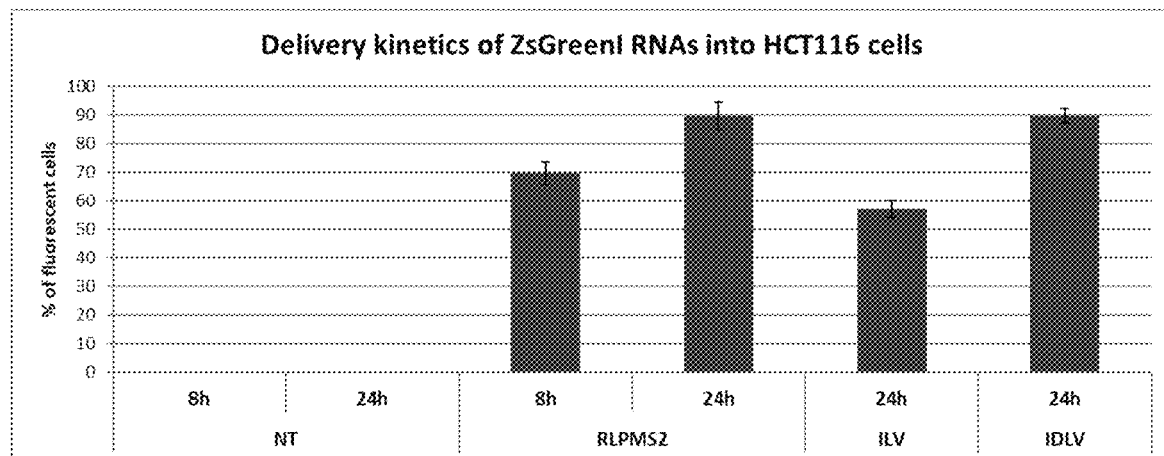
FIG. 8 illustrates the expression kinetics for ZsGreenI in HCT116 cells transduced by lentiviral vectors (ILV, IDLV) and MS2RLP lentiviral particles according to the invention.
Figure 9:
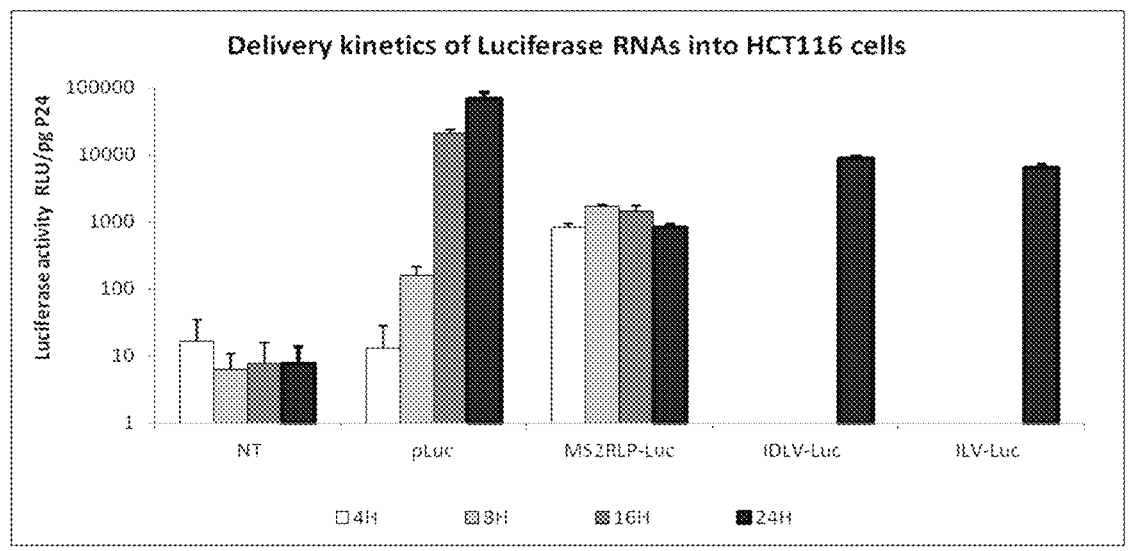
FIG. 9 illustrates the expression kinetics of luciferase in HCT116 cells transduced by lentiviral vectors (ILV, IDLV) and MS2RLP lentiviral particles according to the invention and which were transfected by a luciferase expression plasmid (pLuc)
Figure 10:
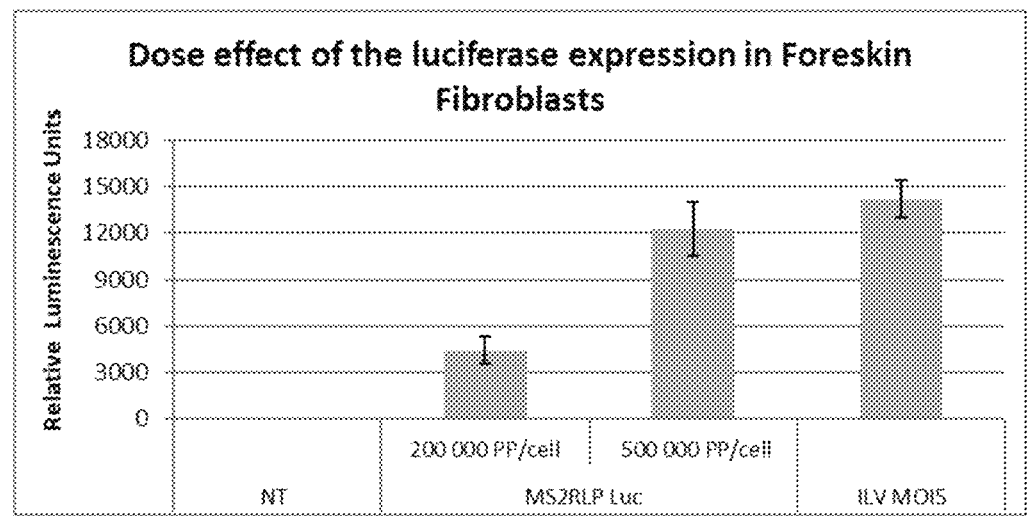
FIG. 10 illustrates the dose effect of the luciferase expression after transduction of Foreskin fibroblasts by ILV vectors and MS2RLP lentiviral particles according to the invention.
Figure 11:
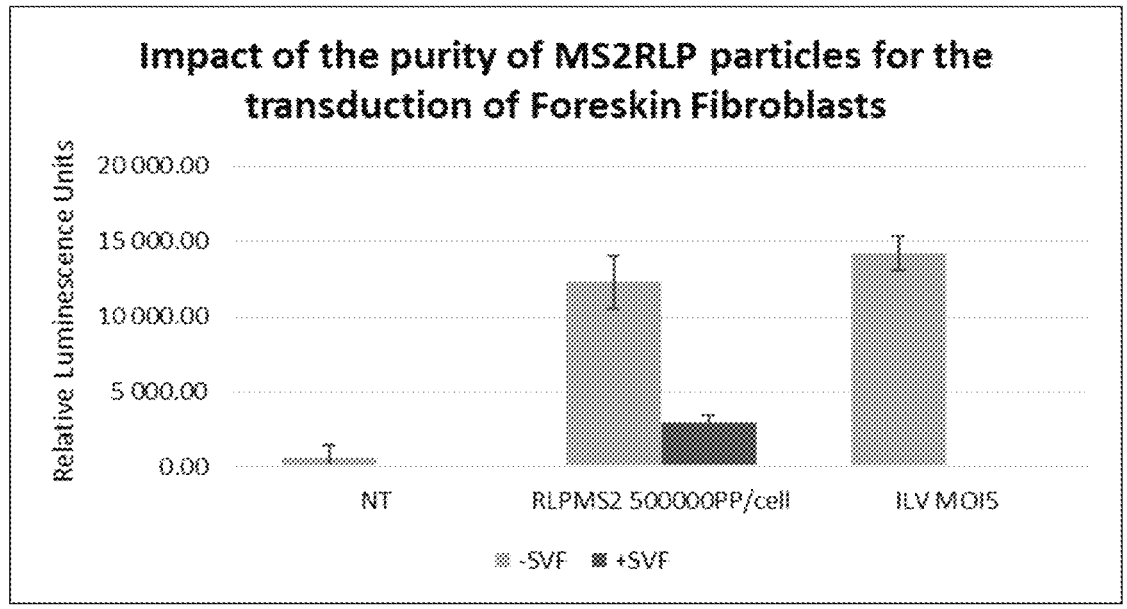
FIG. 11 illustrates the impact of purity (production with or without serum) of a composition of MS2RLP lentiviral particles according to the invention, on the transduction of Foreskin fibroblasts.
Figure 12:
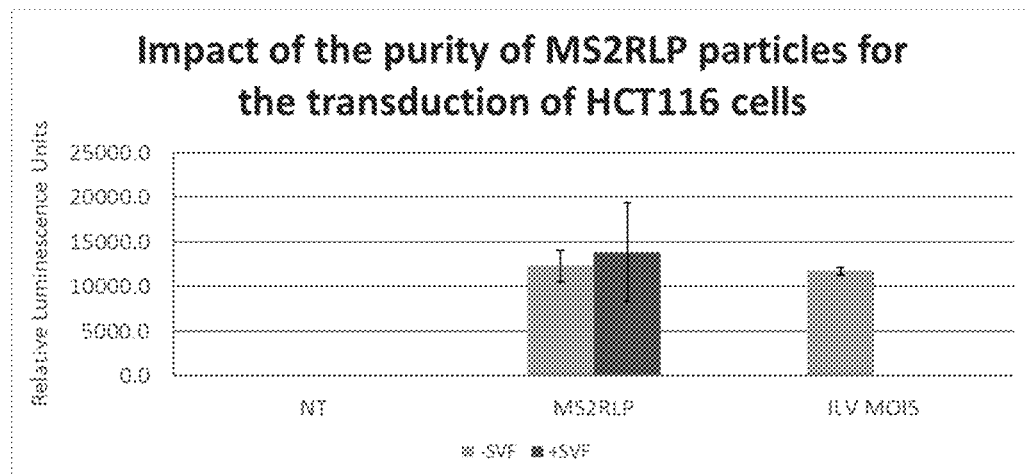
FIG. 12 illustrates the impact of purity (production with or without serum) of a composition of MS2RLP lentiviral particles according to the invention, on the transduction of HCT116 cells.
Figure 13:
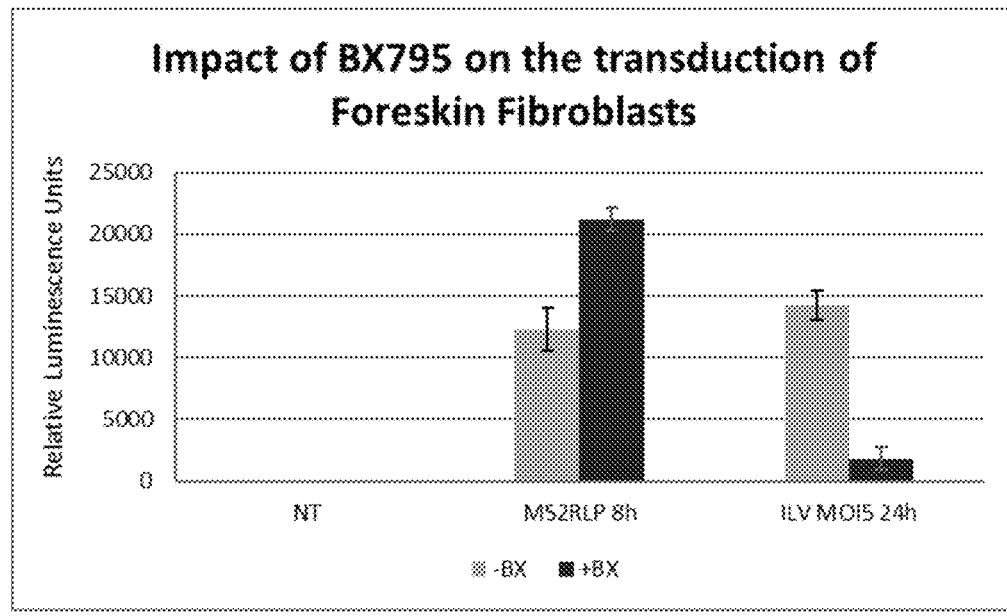
FIG. 13 illustrates the impact of the presence of BX795 at the time of transduction of Foreskin fibroblasts by MS2RLP lentiviral particles according to the invention and ILV vectors.
Figure 14:
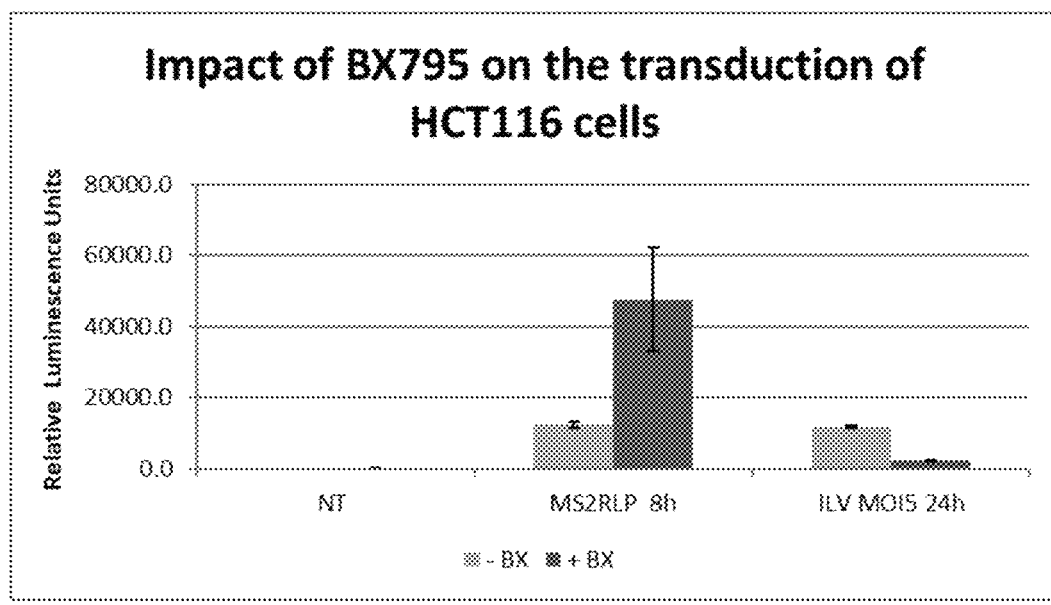
FIG. 14 illustrates the impact of the presence of BX795 at the time of transduction of BX795 cells by MS2RLP lentiviral particles according to the invention and ILV vectors.
Figure 15:
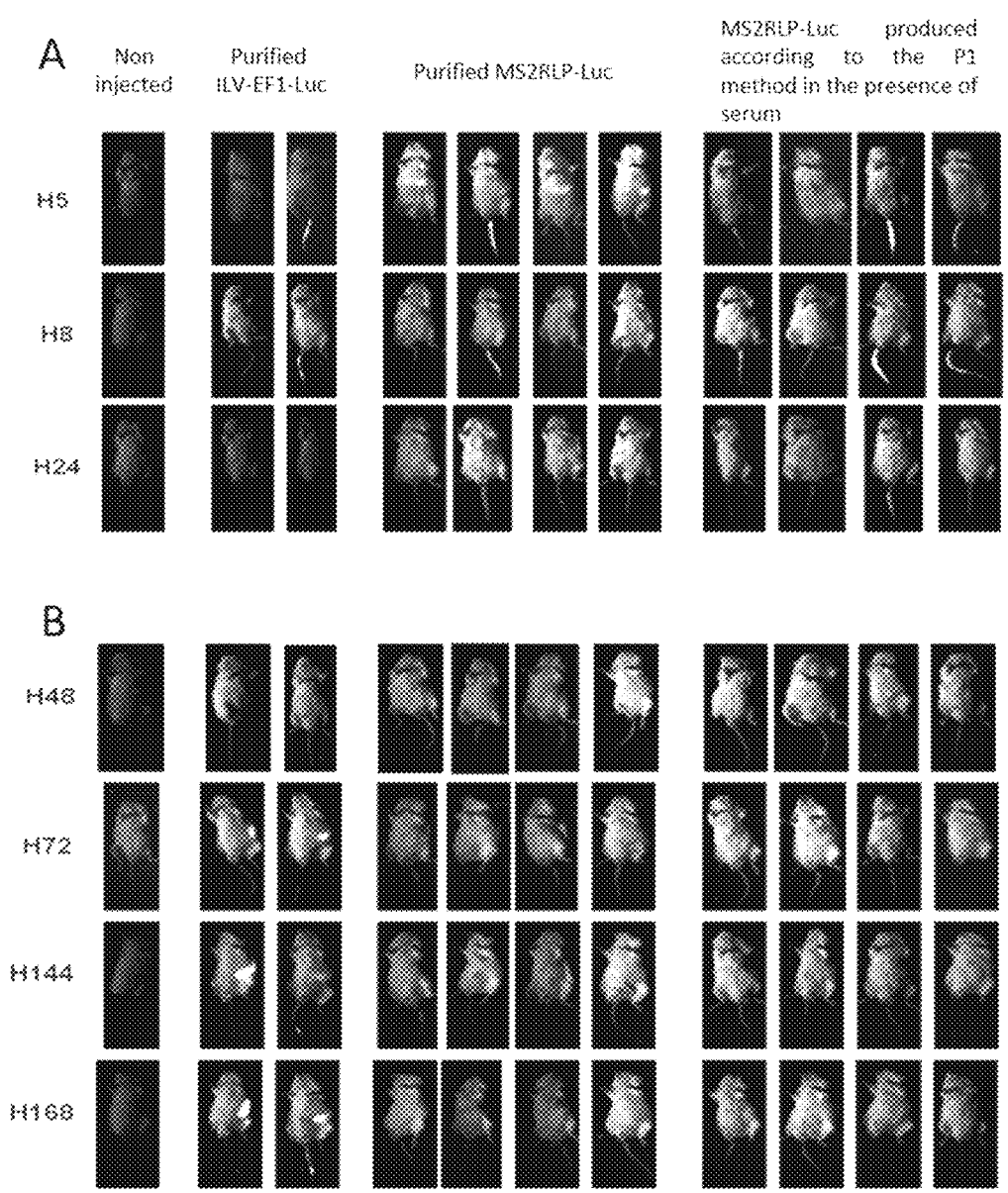
FIGS. 15, 16 and 17 illustrate the expression kinetics of luciferase by bioluminescence in vivo, in mice, after injection of a suspension, whether or not purified, of MS2RLP particles according to the invention and of a purified suspension of ILV vectors.
Figure 16:
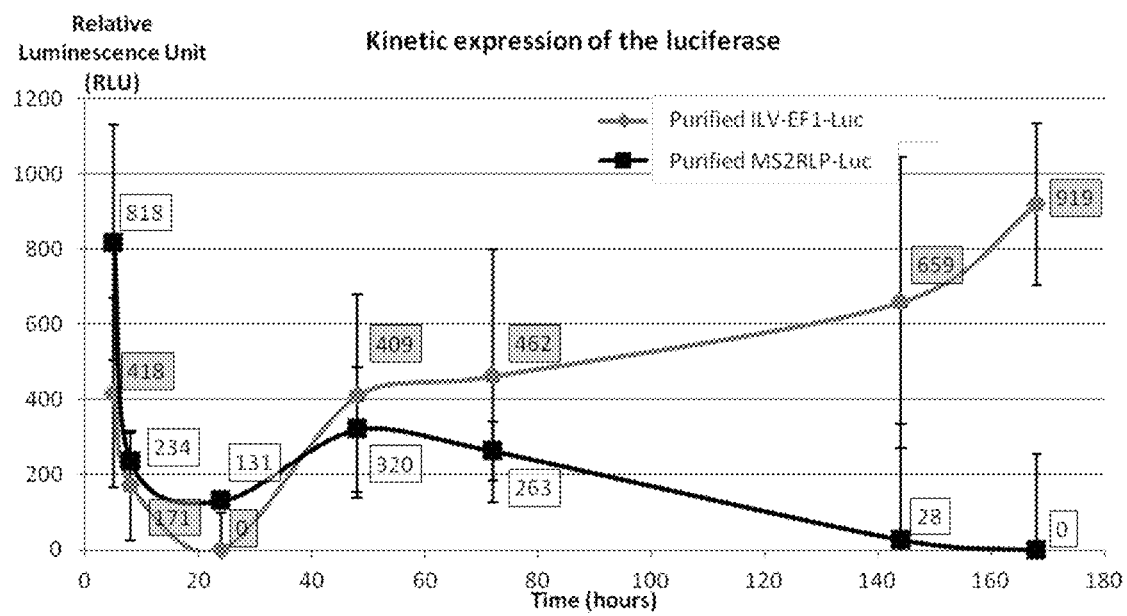
Figure 17:
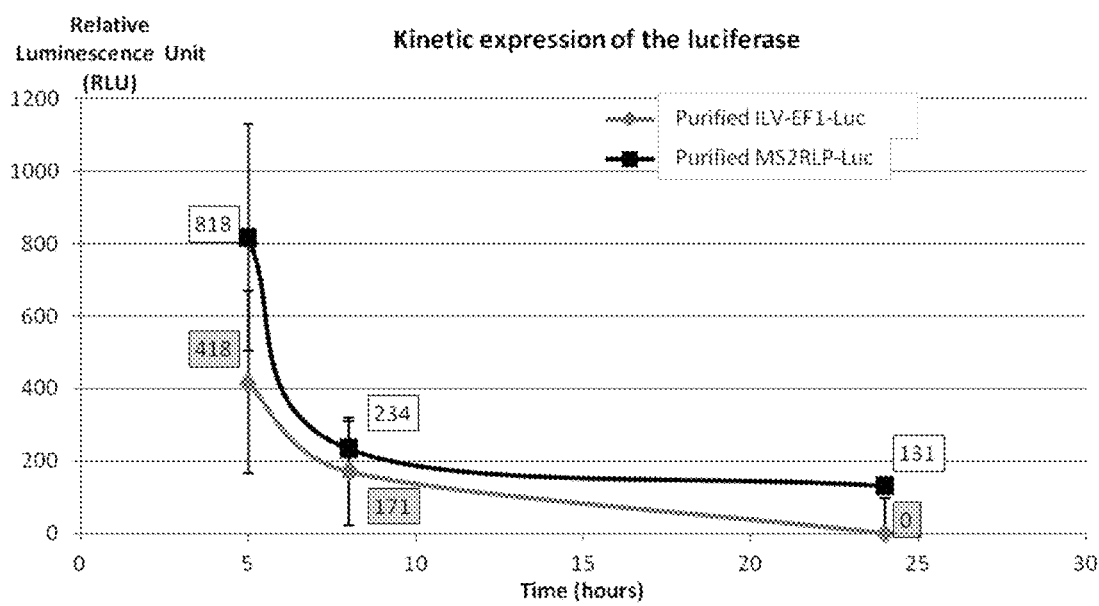
Figure 18:
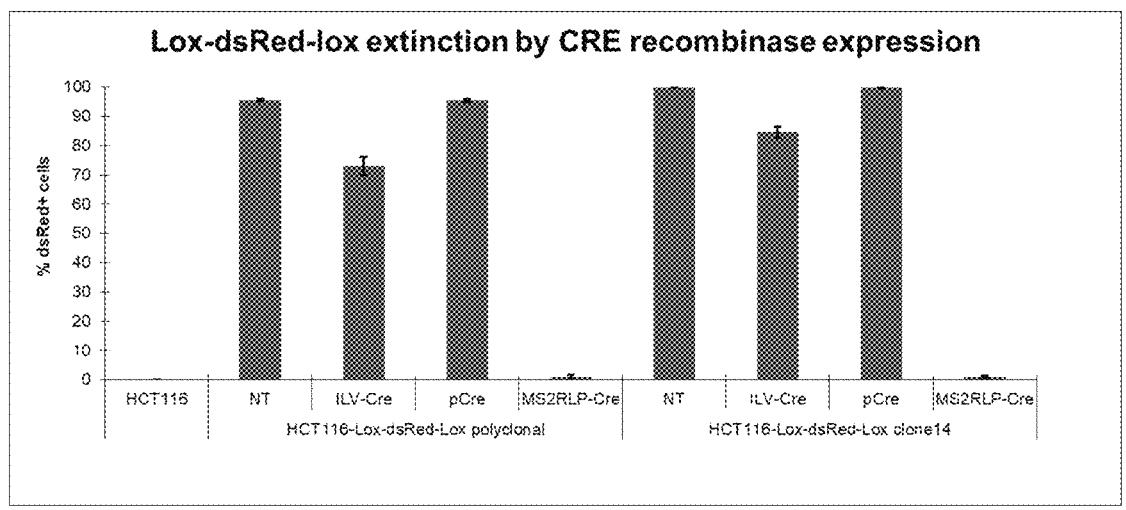
FIG. 18 is a diagram illustrating the extinction of fluorescence in HCT116-Lox-dsRed-Lox cells transduced with ILV vectors or MS2RLP particles according to the invention or transfected with pCre plasmids, enabling the expression of Cre recombinase.
Figure 19:
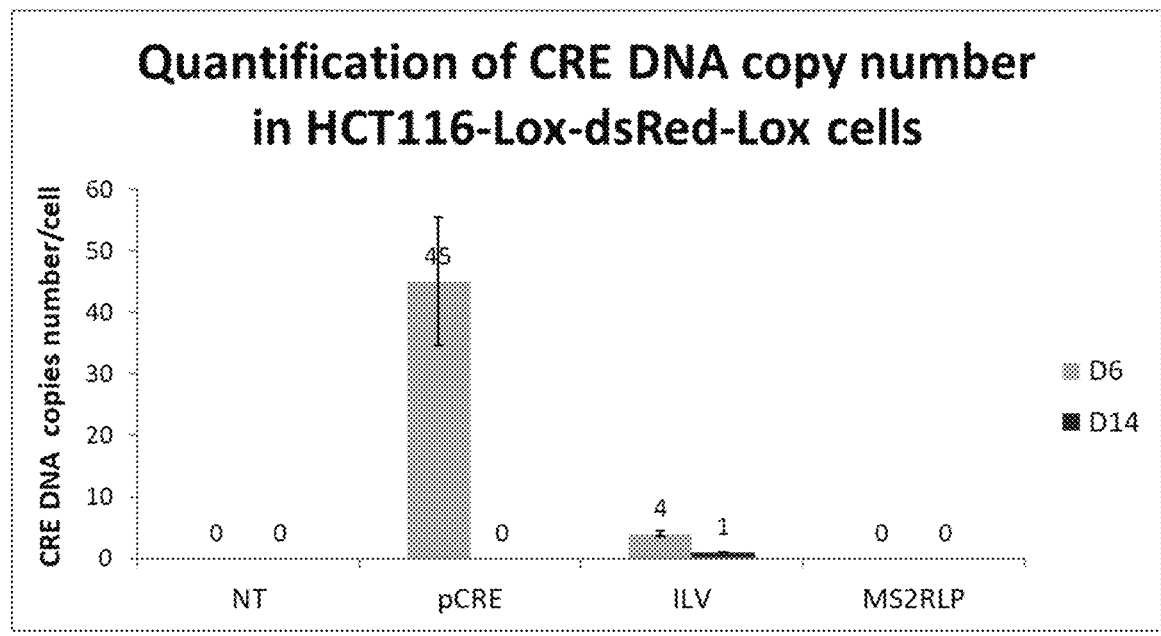
FIG. 19 is a diagram illustrating the quantification of the number of copies of Cre DNA in the HCT116-Lox-dsRed-Lox cells after transduction by ILV vectors or MS2RLP particles according to the invention or transfected with pCre plasmids.
Figure 20:
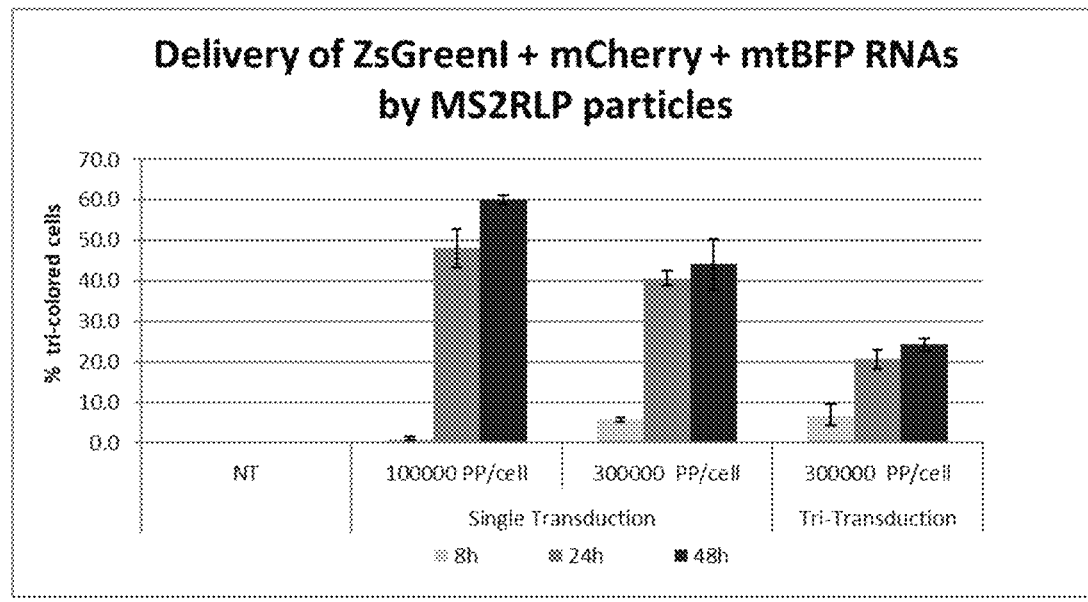
FIG. 20 illustrates the transfer kinetics of several RNAs (RNAs ZsGreenI+mCherry+mtBFP) in HCT116 cells with MS2RLP particles according to the invention.
Figure 21:
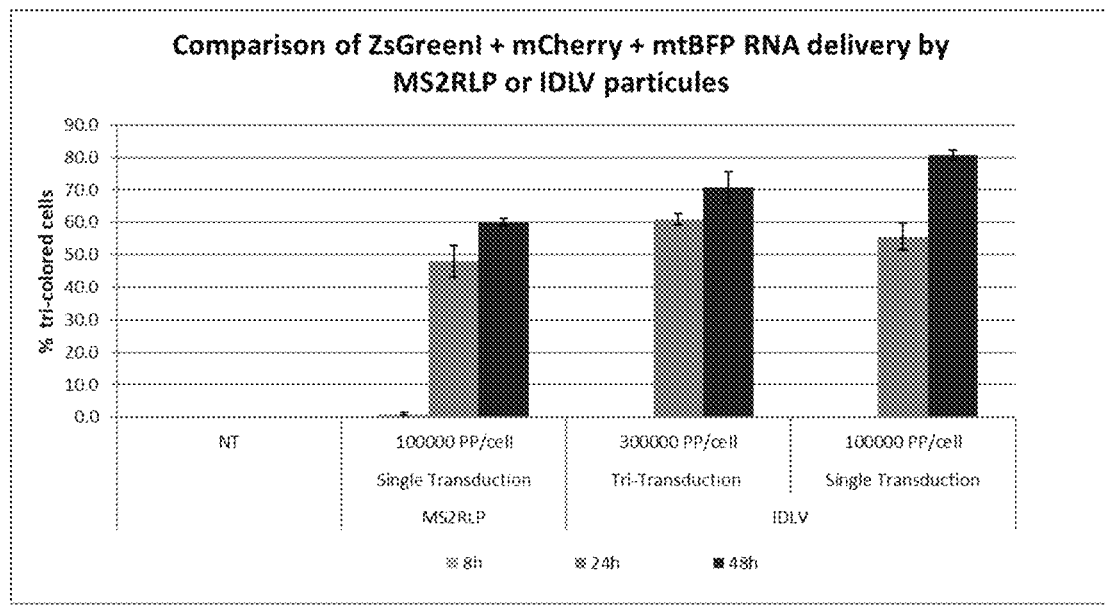
FIG. 21 presents a comparison of the transfer kinetics of several RNAs (RNAs ZsGreenI+mCherry+mtBFP) in HCT116 cells with MS2RLP particles according to the invention or IDLV vectors.
Figure 22:
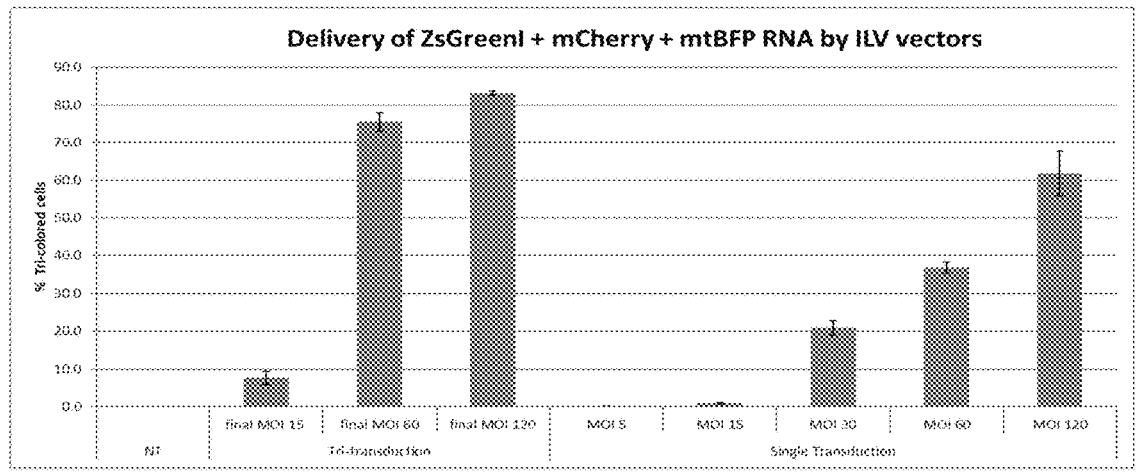
FIG. 22 illustrates the transfer kinetics of several RNAs (RNAs ZsGreenI+mCherry+mtBFP) in HCT116 cells with ILV integrating vectors.
Figure 23:
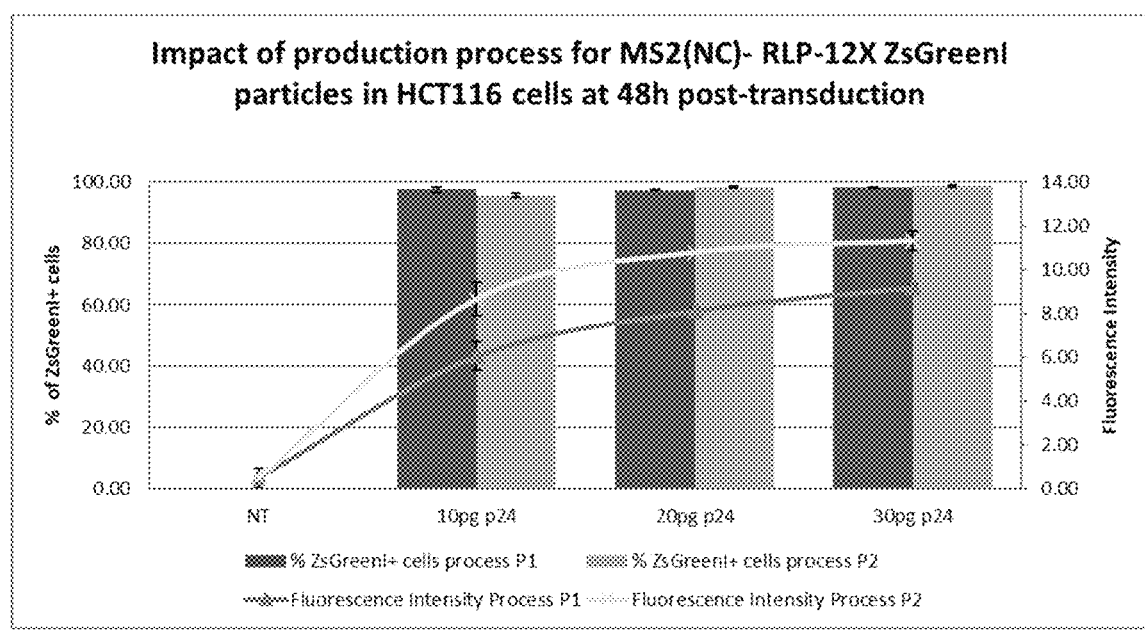
FIG. 23 illustrates the impact of the method for production of MS2(NC)-RLP-12X ZsGreenI particles in HCT116 cells at 48 h post-transfection.
Figure 24:
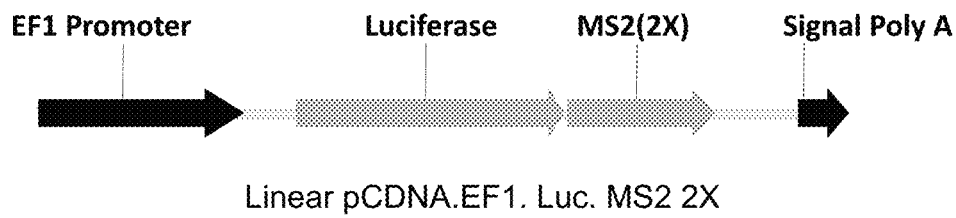
FIG. 24 presents the diagram of the expression plasmid bearing, as RNA sequence of interest, the luciferase used for the production of MS2 (NC)-RLP 2X lentiviral particles, comprising the MS2 stem-loop motif repeated 2 times, according to the invention.
Figure 25:
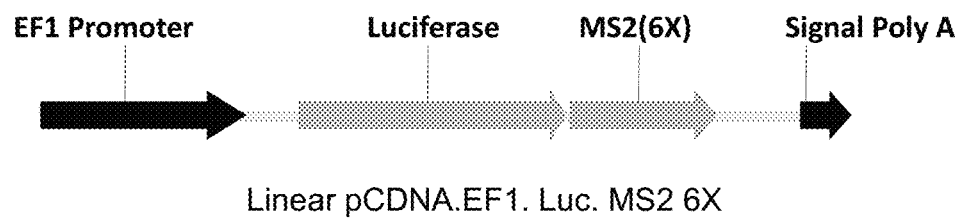
FIG. 25 presents the diagram of the expression plasmid bearing, as RNA sequence of interest, the luciferase used for the production of MS2 (NC)-RLP 6X lentiviral particles, comprising the MS2 stem-loop motif repeated 6 times, according to the invention.
Figure 26:
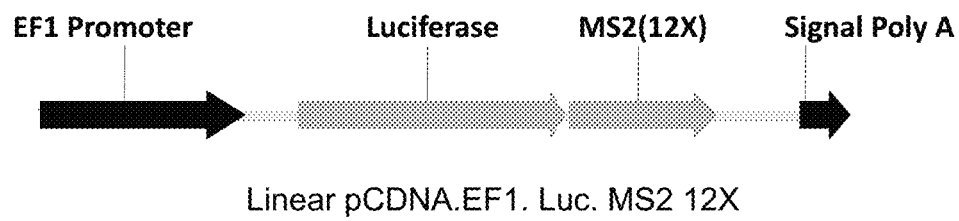
FIG. 26 presents the diagram of the expression plasmid bearing, as RNA sequence of interest, the luciferase used for the production of MS2RLP lentiviral particles, comprising the MS2 stem-loop motif repeated 12 times, according to the invention.
Figure 27:
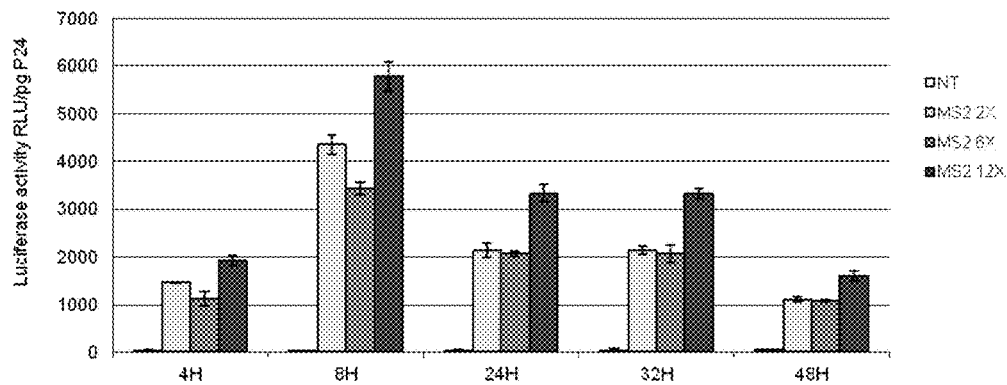
FIG. 27 illustrates the transfer kinetics of Luciferase RNA in HCT116 cells transduced by MS2 (NC)-RLP-Luc lentiviral particles, comprising the MS2 stem-loop motif repeated 2 times, 6 times or 12 times, according to the invention, at a dose of 10 pg p24/cell.
Figure 28:
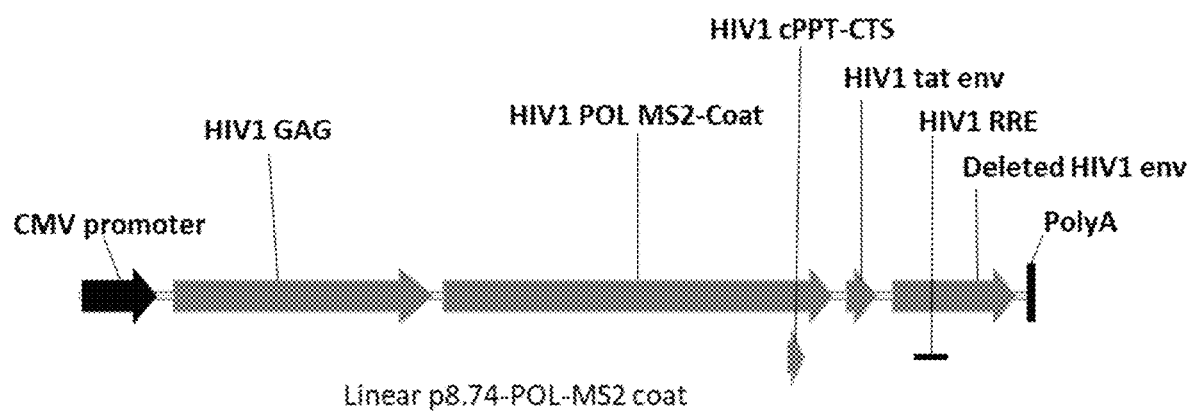
FIG. 28 presents a diagram of the encapsidation plasmid being used for the production of MS2 (IN)-RLP lentiviral particles according to the invention, obtained by the modification of the p8.74 lentiviral encapsidation plasmid in order to insert a binding domain in the integrase sequence as described in FIG. I.
Figure 29:
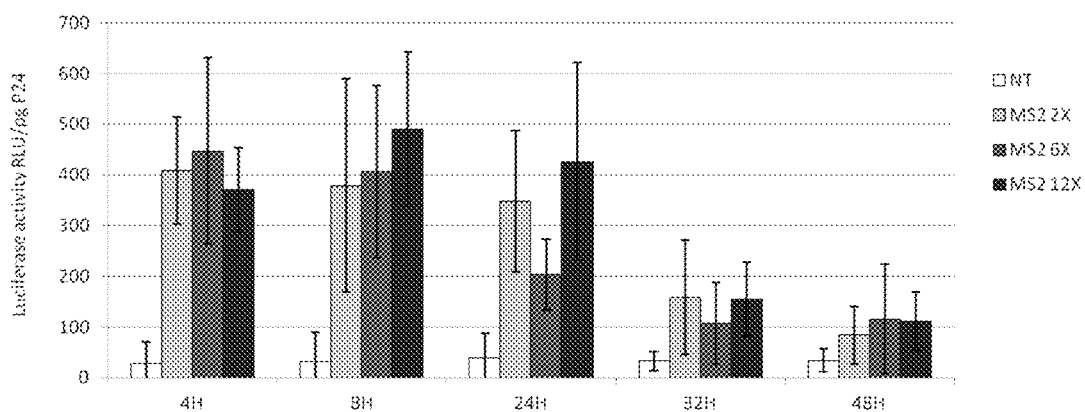
FIG. 29 illustrates the transfer kinetics of Luciferase RNA in HCT116 cells transduced by MS2 (IN)-RLP-Luc lentiviral particles, comprising the MS2 stem-loop motif repeated 2 times, 6 times or 12 times, according to the invention, at a dose of 5 pg p24/cell.
Figure 30:
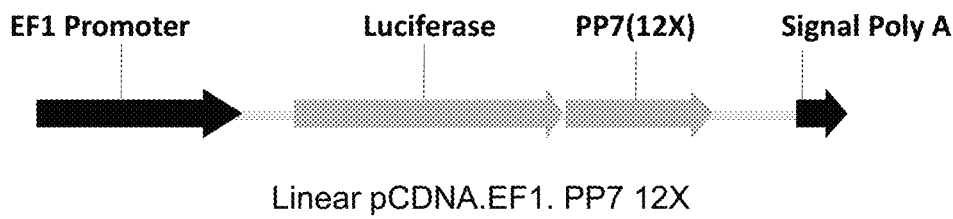
FIG. 30 presents the diagram of the expression plasmid bearing, as RNA sequence of interest, the Luciferase used for the production of PP7RLP lentiviral particles, comprising the PP7 stem-loop motif repeated 12 times, according to the invention.
Figure 31:
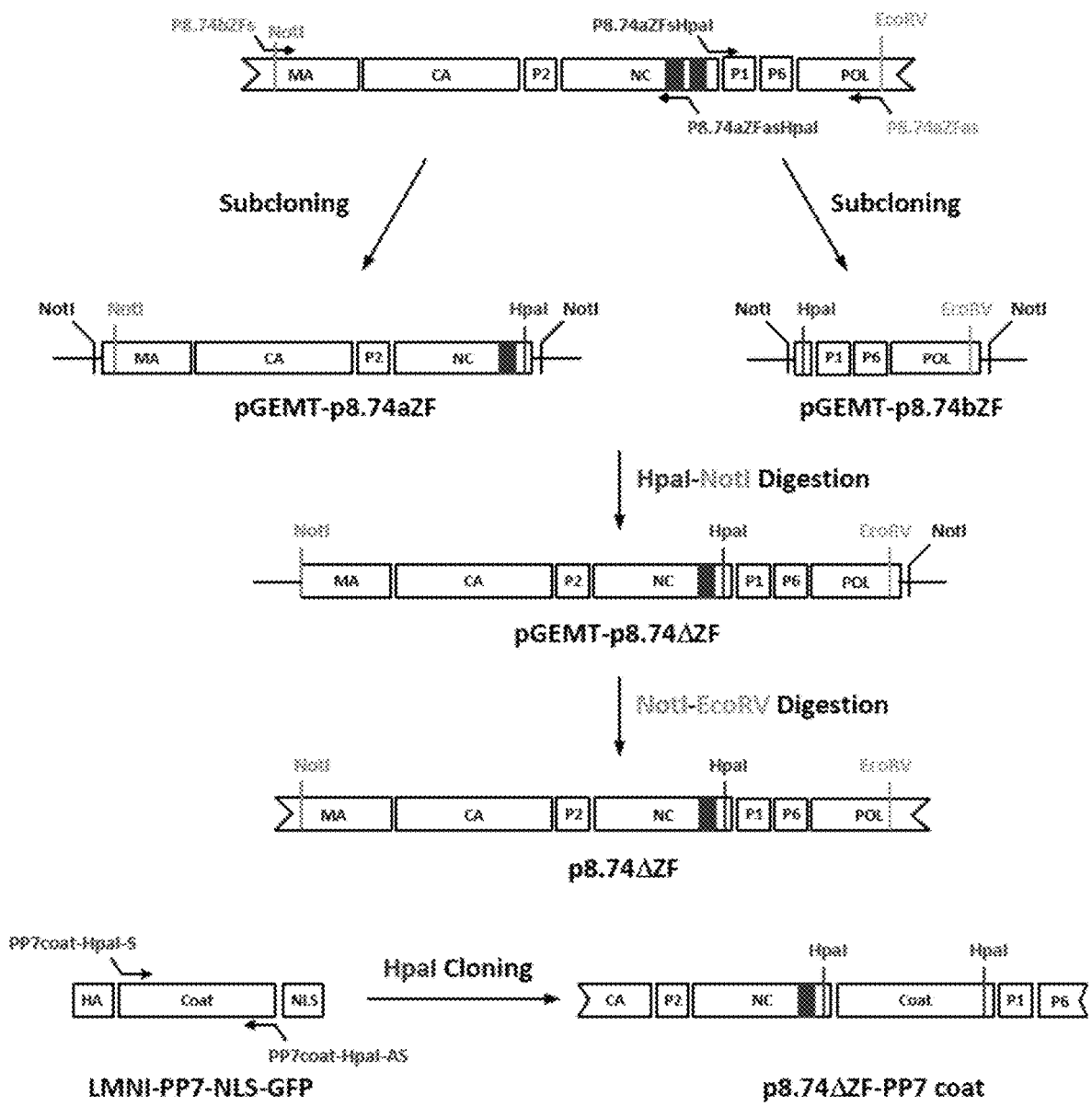
FIG. 31 presents a diagram illustrating the modification of the p8.74 lentiviral encapsidation plasmid in order to insert a Coat PP7 binding domain in the nucleocapsid sequence.
Figure 32:
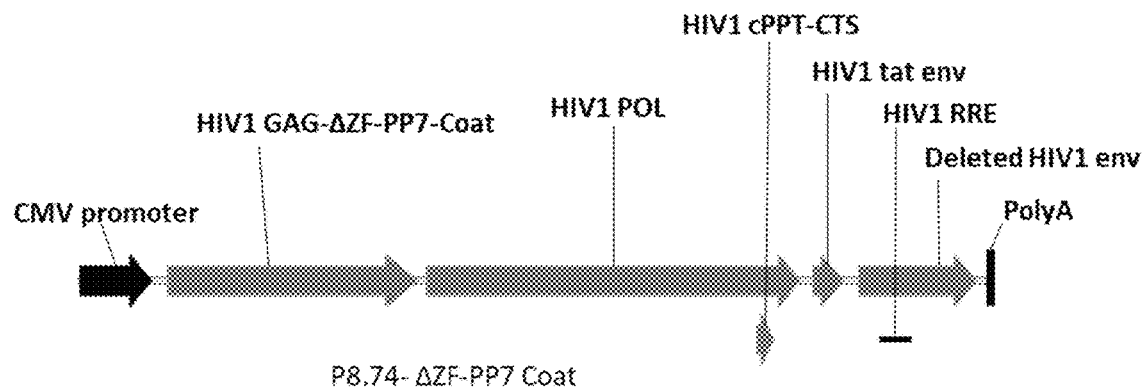
FIG. 32 presents the diagram of the encapsidation plasmid being used for the production of PP7 (NC)-RLP lentiviral particles according to the invention.
Figure 33:
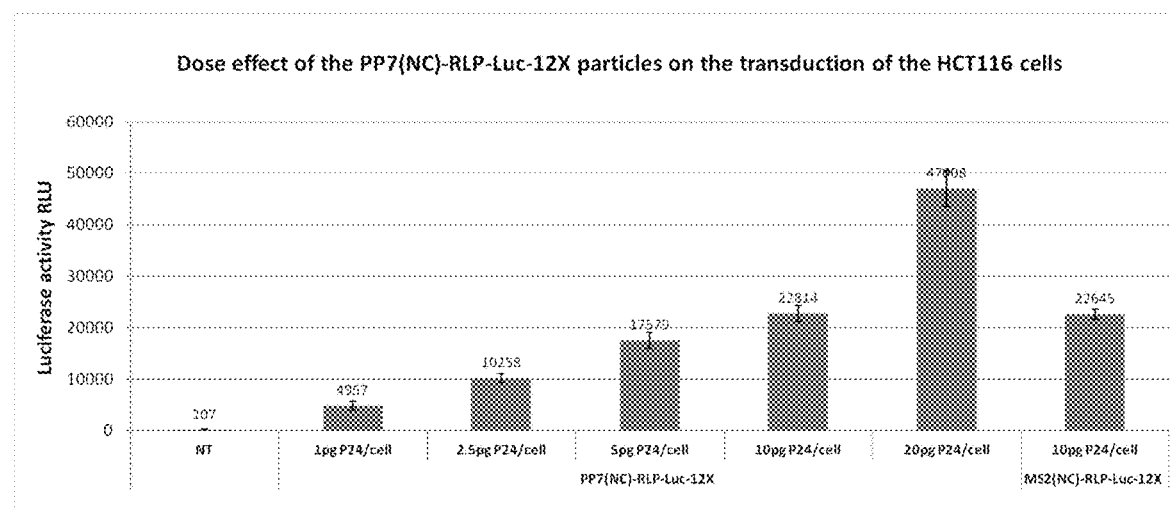
FIG. 33 illustrates the dose effect of PP7 (NC)-RLP-Luc 12X particles according to the invention on the transduction of HCT116 cells.
Figure 34A:
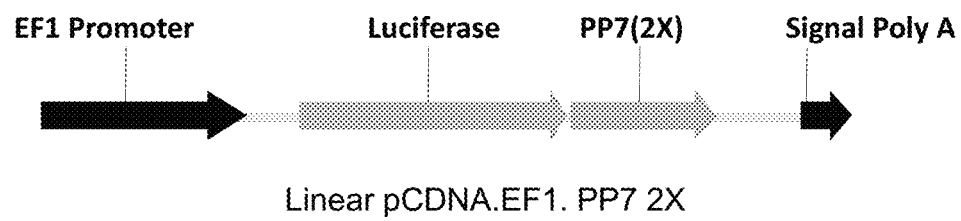
FIGS. 34A and 34B present diagrams of the expression plasmid with the PP7 stem-loop motif repeated 2 times, comprising the expression cassette for Luciferase (FIG. 34A) or for a fluorescent reporter (FIG. 34B) for the production of PP7 (NC)-RLP 2X or PP7 (IN)-RLP 2X particles according to the invention.
Figure 34B:
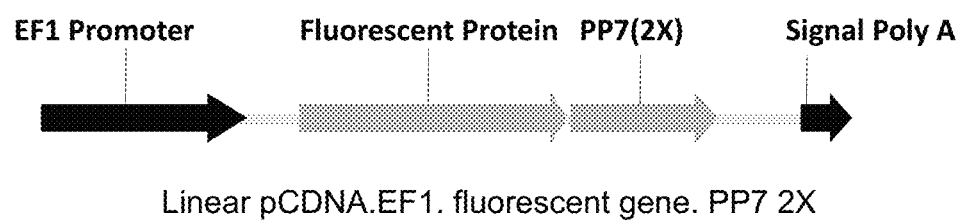
Figure 35:
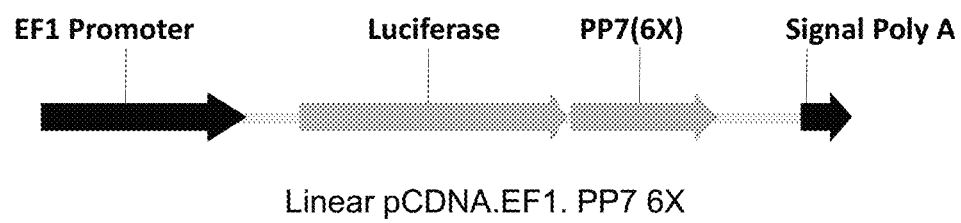
FIG. 35 presents a diagram of the expression plasmid for Luciferase with the PP7 stem-loop motif repeated 6 times for the production of PP7 (NC)-RLP 6X or PP7 (IN)-RLP 6X particles according to the invention.
Figure 36:
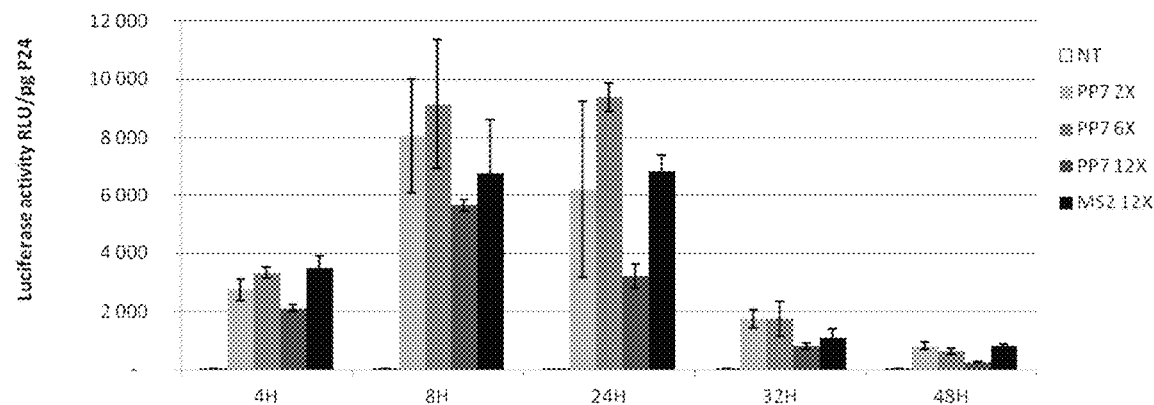
FIG. 36 illustrates the transfer kinetics of Luciferase RNA in HCT116 cells transduced by PP7 (NC)-RLP-Luc particles, of which the PP7 stem-loop motif is repeated 2 times, 6 times or 12 times, at a dose of 10 pg p24/cell.
Figure 37:
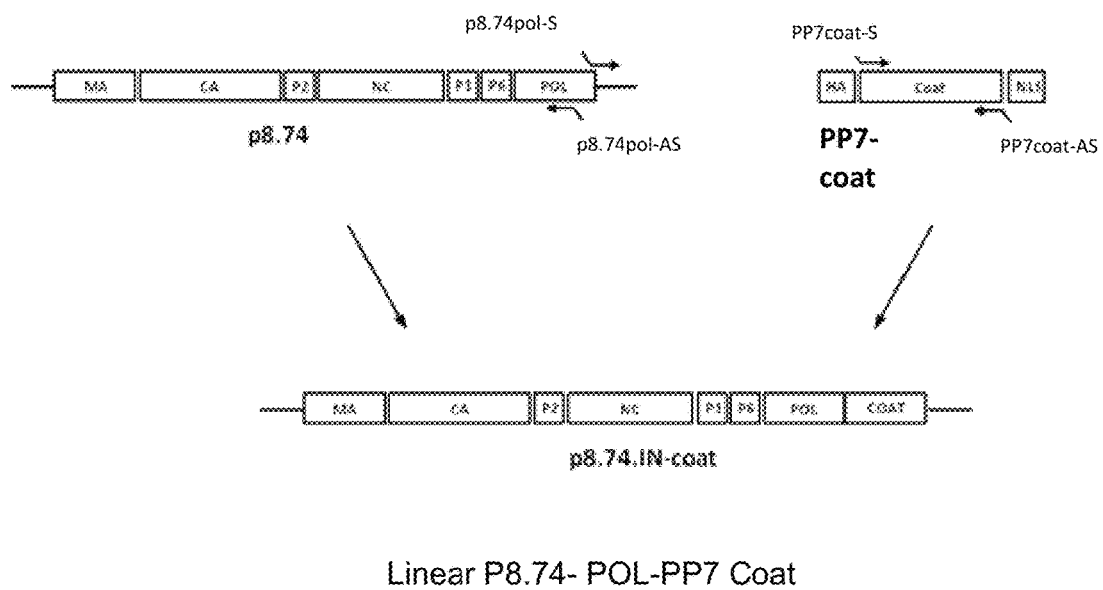
FIG. 37 presents a diagram of the modification of the p8.74 lentiviral encapsidation plasmid in order to insert a binding domain in the integrase sequence.
Figure 38:
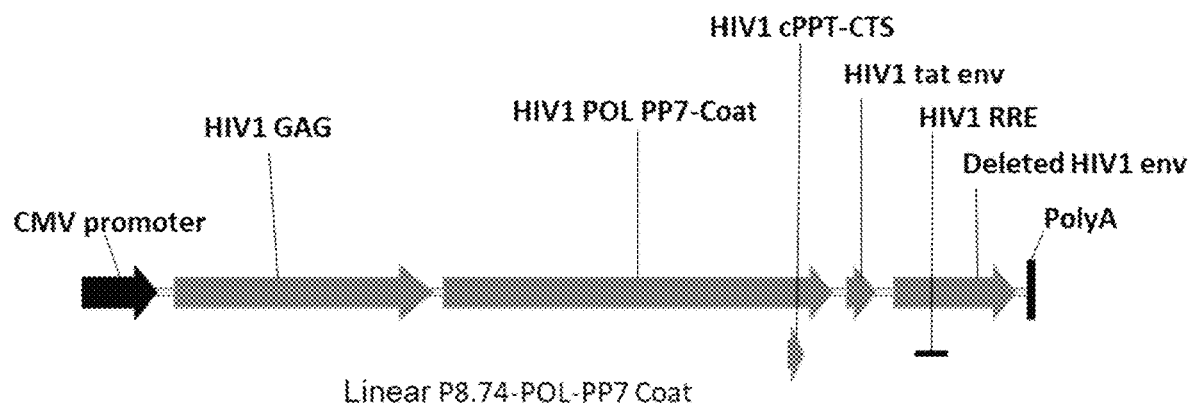
FIG. 38 presents a diagram of the encapsidation plasmid used for the production of PP7 (IN)-RLP lentiviral particles according to the invention, obtained by modifying the p8.74 lentiviral encapsidation plasmid presented in FIG. 37.
Figure 39:
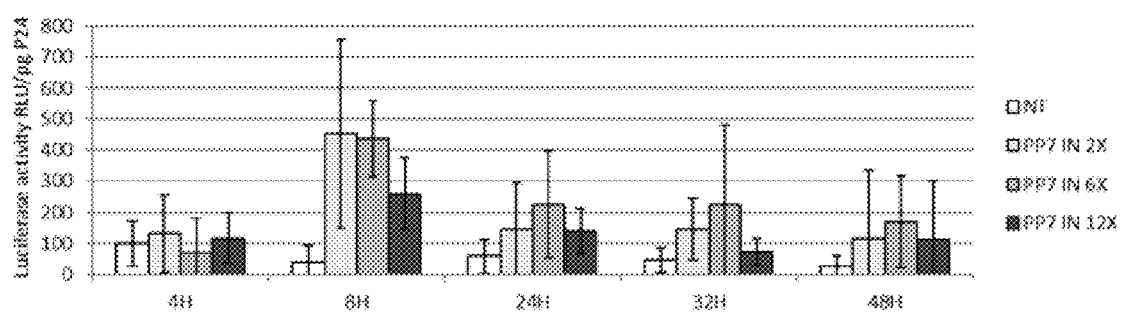
FIG. 39 illustrates the transfer kinetics of Luciferase RNA in HCT116 cells transduced by PP7 (IN)-RLP-Luc lentiviral particles, comprising the PP7stem-loop motif repeated 2 times, 6 times or 12 times, according to the invention, at a dose of 2.8 pg p24/cell.
Figure 40:
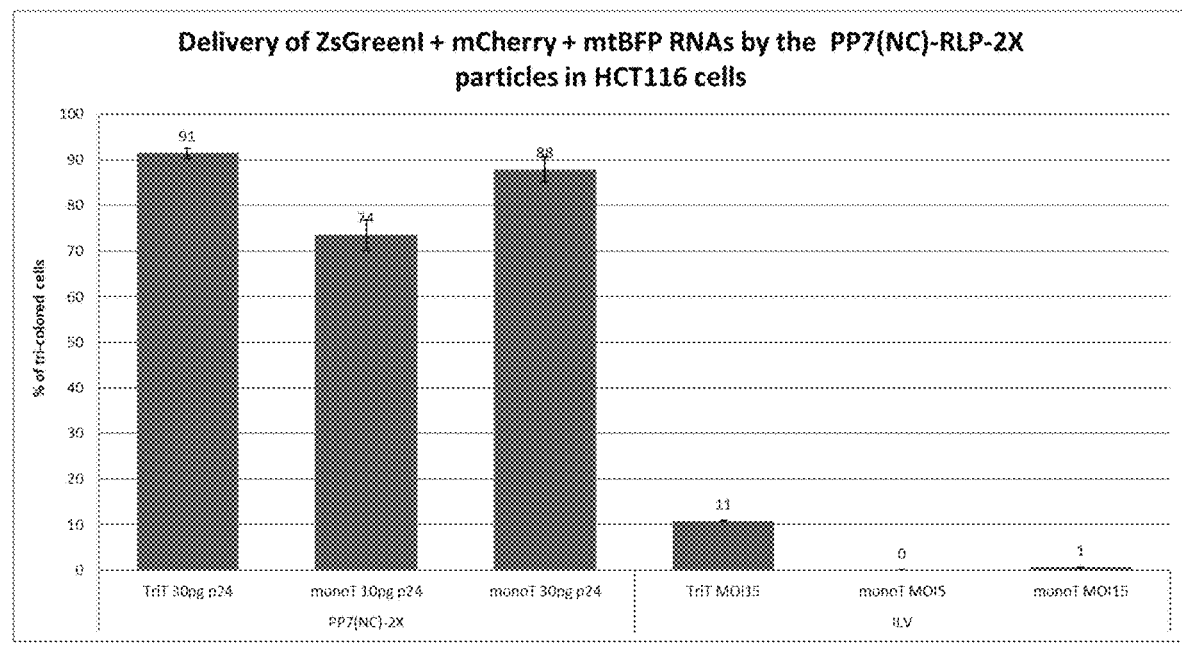
FIG. 40 illustrates the transfer of ZsGreenI+mCherry+ mtBFP RNAs by the PP7 (NC)-RLP 2X particles into HCT116 cells.

I. Equipment and Methods
1. Plasmid Construction
1.1 Plasmids for the Production of MS2RLP Lentiviral Particles Expression plasmid for a sequence of interest: The expression plasmid bears a promoter-sequence of interest-polyA expression cassette (see FIG. II) with or without an RNA stabilizing or intronic sequence. In order to transport the mRNAs into the lentiviral particles, 12 repetitions of the stem-loop motif of the MS2 RNA (ctagaaaacatgaggatcacccatgtctgcag, SEQ ID No. 1) were inserted inside an expression cassette downstream of the reporter gene. The promoter used may be that of CMV (FIG. IIa) or EF1 (FIGS. IIb and IIc) but other promoters may be used. The sequence of interest may be a DNA coding a reporter protein such as native Firefly luciferase (FIG. IIa), a green (ZsGreenI), red (mCherry) or blue (mtBFP) fluorescent protein (FIG. IIb), or a cDNA coding a protein, for example the CRE protein (FIG. IIc). The sequence of interest may also be that of an shRNA, an miRNA, an sgRNA, an LncRNA or of an circRNA.

Encapsidation plasmid: The lentiviral particle was modified to contain the Coat protein sequence of the bacteriophage MS2 within the nucleocapsid protein, instead of and in place of the second Zn finger domain The p8.74 encapsidation plasmid (FIG. III), carrier of the genes coding the structural and functional proteins (Gag, Pol), used for the production of the MS2RLP particles is modified according to the strategy illustrated by FIG. IIIa: this p8.74 plasmid is used to generate, by PCR assembly, a plasmid lacking the second zinc finger of the p8.74ΔZF nucleocapsid protein. The second zinc finger is substituted by the Coat protein of the phage MS2 by HpaI cloning, to generate the p8.74ΔZF-MS2-Coat plasmid. The construction illustrated in FIG. IIIb is thereby obtained. The sequence coding Pol may be deleted or mutated in some functional elements for example such as the sequence coding the reverse transcriptase (RT) or the integrase (IN) without altering the function of the MS2RLPs.

Envelope plasmid (pENV): This plasmid carries the gene coding an envelope protein, which may be the VSVG coding the envelope protein of the Vesicular stomatitis virus (FIG. IV).

1.2 Plasmids for the Production of Integrating Lentiviral Vectors ILV

Expression plasmid for a sequence of interest: The expression plasmid carries a promoter-sequence of interest expression cassette (FIG. V). This plasmid may contain other elements such the WPRE native sequence (WPRE standing for Woodchuck Hepatitis Virus Post-transcriptional Regulatory Element) or the cPPT/CTS sequence. The viral pathogenicity is eliminated by the substitution of regions of the viral genome required for the retroviral replication by the transgene.

Encapsidation plasmid: The p8.74, encapsidation plasmid, which carries the genes coding for the structural and functional proteins (Gag, Pol), is used for the production of the integrating lentiviral vectors (FIG. VI).

Envelope plasmid (pENV): This plasmid is identical to the envelope plasmid used for the production of MS2RLP lentiviral particles (FIG. IV).

1.3 Plasmids for the Production of Integration-Deficient Lentiviral Vectors IDLVs: Mutant D64L The 3 plasmids are the same as those described in point 1.2 except for the encapsidation plasmid which comprises a D64L mutation of the pol sequence coding for the integrase (FIG. VII). This mutation on a single amino acid induces inhibition of the integration (Nightingale et al., 2006 and Apolonia et al., 2007). The D64L mutation on the integrase (IN) was introduced in the p8.74 plasmid by site-directed mutagenesis. The mutation was verified by sequencing.

1.4 DLuc and DCre Plasmids

These expression plasmids are similar to those used for the production of the ILV and IDLV vectors (FIG. Vb for pLuc and FIG. Vc for pCre), used directly in transfection for control.

2. Batch Production

After the transfection of the plasmids into cells, the supernatants are harvested and used crude or concentrated/purified according to the method described in application WO 2013/014537.

2.1 Production of the Lentiviral Vectors and Lentiviral Particles

The productions are carried out in a 10-stack CellSTACK (6360 cm$^2$, Corning) with HEK293T cells (ATCC, CRL-11268), cultured in Dulbecco's Modified Eagle's Medium (DMEM, Gibco, Paisley, UK) suplemented with 1% penicillin/streptomycin and 1% ultraglutamine (PAA) at 37° C. in moist atmosphere with 5% $CO_2$. For the serum impact study assay, the DMEM is suplemented with 10% SVF. In particular, no induction with sodium butyrate is carried out. For each batch (MS2RLP, ILV and IDLV), the transfection mixture is composed of the following three plasmids:

One of the expression plasmids described above, depending on whether what is formed is a particle (MS2RLP) or a vector (ILV, IDLV), p8.74ΔZF Coat (MS2RLP), p8.74 (ILV) or p8.74 mutated in position D64L (IDLV), and pENV bearing the envelope VSV-G.

24 hours after standard transfection with calcium phosphate, the culture supernatant is replaced with fresh unsupplemented DMEM medium. The cells are incubated at 37° C./5% CO2. After changing the medium, the supernatant is harvested four times (32 h, 48 h, 56 h and 72 h post transfection). Each collection is clarified by 5 min centrifugation at 3000 g before being microfiltered on a 0.45 µm filter (Stericup, Millipore). All the collections are then pooled to compose the crude supernatant.

2.2 Concentration and Purification of the Lentiviral Vectors and Lentiviral Particles The vectors and particles are concentrated and purified according to one of the following two methods:

The method P1 is directed to performing frontal ultrafiltration of the supernatant on centrifugation central units.

The P2 method is directed to performing tangential ultrafiltration then diafiltration of the supernatant. The crude supernatant is concentrated and purified by tangential ultrafiltration via the use of polysulfone hollow-fiber cartridges. The supernatant is treated by diafiltration for 20 diavolumes in continuous mode against DMEM or TSSM buffer. After the diafiltration, the retentate is collected then concentrated again by frontal ultrafiltration on central centrifugation units.

3. Titration 3.1 Titration of the Functional Particles by qPCR

The HCT116 cells (ATCC, CCL-247) are seeded in 96-well plates in 100 µL of DMEM supplemented with 10% SVF, 100 µg/mL Stretomycin, 100 U/mL Penicillin and 2 mM L-Gln then incubated 24 h to 37° C./5% CO2. Six serial dilutions are carried out for each vector as well as for an internal calibration reference. The cells are transduced by serial dilutions in the presence of Polybrene® 8 µg/mL (Sigma) then incubated for three days 37° C./5% CO2. For each series of samples, one well of non-transduced cells is added as control. The cells are next trypsinized and the titer (Transduction Unit/mL) is determined by qPCR after extraction of the genome DNA using the Nucleospin tissue gDNA extraction kit (Macherey-Nagel). The titer obtained (TU/mL) by qPCR is normalized with the internal calibration reference of which the titer was determined in advance by FACS.

3.2 Quantization of the Physical Particles by P24 ELISA Test

The p24 capsid protein is directly detected in the viral supernatant using and following the recommendations for the HIV-1 p24 ELISA kit (Perkin Elmer). The p24 protein captured is complexed with a biotinylated polyclonal antibody, then detected by a streptavidin-HRP peroxidase conjugate. The resulting complex is detected by spectrophotometry after incubation with the substrate ortho-phenylenediamine-HCl (OPD) which produces a yellow coloration that is directly proportional to the amount of p24 captured. The absorbance of each well is quantified using the microplate reader Synergy H1 Hybrid (Biotek) and calibrated against absorbance of a p24 protein calibration reference range. The viral titer expressed in physical particles per mL is calculated from the p24 protein concentration obtained knowing that 1 pg of p24 protein corresponds to $10^4$ physical particles.

4. Monotransduction

This example is directed to developing the conditions for monotransduction by the lentiviral vectors or the lentiviral particles produced above.

5. Expression Kinetics for ZsGreenI

The HCT116 cells seeded the previous day with 25000 cells/cm2 in a 24-well plate (Corning) are transduced to 100000 PP/cell in the presence of 8 µg/mL of Polybrene®. At 8 h and 24 h post-transduction, the cells are trypsinized and analyzed by flow cytometry to measure the percentage of fluorescent cells. Each assay is carried out in triplicate.

6. Expression Kinetics for Luciferase 6.1 HCT116 Cells

The HCT116 cells (ATCC, CCL-247) are seeded in 6 or 24-well plates and incubated for 24 h at 37° C./5% CO2. The transduction by ILV or IDLV vectors or MS2RLP particles is carried out in the presence of 4 µg/mL Polybrene. The transduction supernatant is eliminated 4 hours after and replaced by fresh supplemented growth medium. From 4 h to 24 h post-transduction, the cells are harvested and the expression of the luciferase is analyzed using the kit OneGlo Luciferase assay (Promega) following the recommendations of the supplier and using the Synergy H1 Hybrid microplate reader (Biotek). This test is carried out in triplicate. In parallel, the HCT116 cells are transfected with the pLuc plasmid. For this, 50000 HCT116 cells are transfected with 2.6 µg of pLuc plasmid using PEI PRO® (Polyplus Transfection).

6.2 Foreskin Fibroblasts

The Foreskin fibroblasts seeded the previous day with 10,000 cells/cm$^2$ in a 6-well plate (Corning) are transduced in the presence of 4 µg/mL of Polybrene®. The cells were transduced to 200 000 and 500 000 PP/cell with the MS2RLP-Luc, or with MOI5 with a Luc Integrating lentiviral vector.

The cells transduced by the MS2RLP-Luc are trypsinized 8 h post-transduction and passed into opaque black-bottomed 96-well plates in 100 µL of complete medium. The cells transduced by the ILV Luc are trypsinized 24 h post-transduction and passed into opaque black-bottomed 96-well plates in 100 µL of complete medium. 3 minutes prior to reading in the luminometer, 100 µL of the reagent One Glo Luciferase (Promega) are added per well to analyze.

6.3 In Mice

Expression kinetic measurements for luciferase by bioluminescence in vivo were conducted.

Three groups of Balb/c male mice were compared, a first group received a suspension of purified rLV-EF1-Luc integrating type lentiviral viral (n=2), a second group received a suspension of MS2RLP-Luc particles (n=4) produced according to the P2 method, and a last group received a suspension of MS2RLP-Luc particles (n=4) produced according to the method P1. A non-injected animal served as negative control for determining background noise.

The measurements are carried out from 5 h to 24 h (FIG. XV A), and from 48 h to 168 h (FIG. XV B) after systemic injection. Each measurement of the expression of luciferase was made 15 minutes after intra-peritoneal injection of 300 mg/kg de D-luciferine (Promega) with an Andor camera, and the Soils imaging software. The acquisition time is 5 minutes and the resulting images were processed and normalized with the ImageJ software. FIG. XV shows the images of each animal at the given times. The graphs (FIGS. XVI and XVII) represent the measurements of luciferase expression, in relative luminescence units (RLU) at these times.

7. Impact of the Purity of the Particles for the Transduction 7.1 Foreskin Fibroblasts The Foreskin fibroblasts seeded the previous day with 10000 cells/cm$^2$ in a 24-well CellBind (Corning) are transduced in the presence of 4 µg/mL of Polybrene®. The cells were transduced at 500 000 PP/cell with two types of quality of supernatant: batch produced in the presence of serum then obtained with the P2 method vs. batch produced without serum then obtained with the P2 method. At 8 h post-transduction, the cells are trypsinized and passed into opaque black-bottomed 96-well plates in 100 µL of complete medium. 3 minutes prior to reading in the luminometer, 100 µL of the reagent One Glo Luciferase (Promega) are added per well to analyze.

7.2 HCT116 Cells

The cells seeded the previous day with 25000 cells/cm$^2$ in a 24-well CellBind (Corning) are transduced in the presence of 4 µg/mL of Polybrene®. The cells were transduced at 100000 PP/cell with two types of quality of supernatant: batch produced in the presence of serum then obtained with the P1 method vs. batch produced without serum then obtained with the P1 method. At 8 h post-transduction, the cells are trypsinized and passed into opaque black-bottomed 96-well plates in 100 µL of complete medium. 3 minutes prior to reading in the luminometer, 100 µL of the reagent One Glo Luciferase (Promega) are added per well to analyze.

8. Impact of BX795

8.1 Foreskin Fibroblasts

The Foreskin fibroblasts seeded the previous day with 10,000 cells/cm$^2$ in a 6-well CellBind (Corning) are transduced in the presence of 4 µg/mL of Polybrene®. The cells were transduced to 500000 PP/Cell for the MS2RLP particles, and MOI 5 for the ILVs. At 8 h post-transduction, the cells are trypsinized and passed into opaque black-bottomed 96-well plates in 1001 µL of complete medium. 3 minutes prior to reading in the luminometer, 100 µL of the reagent One Glo Luciferase (Promega) are added per well to analyze.

8.2 HCT116 Cells

HCT116 cells seeded the previous day with 25,000 cells/cm$^2$ in a 6-well CellBind (Corning) are transduced in the presence of 4 µg/mL of Polybrene®. The cells were transduced to 100000 PP/Cell for the MS2RLP, and MOI 5 for the ILVs. At 8 h post-transduction, the cells are trypsinized and passed into opaque black-bottomed 96-well plates in 100 µL of complete medium. 3 minutes prior to reading in the luminometer, 100 µL of the reagent One Glo Luciferase (Promega) are added per well to analyze.

9. In Vitro Expression of the CRE Recombinase

In a first phase, the HCT116 cells (ATCC, CCL-247) are transduced by the ILV-EF1-Lox-dsRed-Lox lentiviral vector at MOI120 in the presence of 4 µg/mL Polybrene. Six days later, this polyclonal population is cloned using limiting dilution by seeding the cells in 96-well plates in a ratio of 0.5 cells per well. The HCT116-lox-dsRed-lox-clone 14 monoclonal line was selected by cytometry (MACS Quant VYB, Miltenyl), on the basis of the expression level of the dsRed.

In a second phase, the polyclonal and monoclonal cell lines were transduced with ILV-Cre vectors at MOI 5 or MS2RLP-Cre particles at a dose of 2$^5$ Physical Particles (PP)/cell in the presence of 4 µg/mL of Polybrene®.

The HCT116-Lox-dsRed-Lox monoclonal and polyclonal cells transduced by the MS2RLP-Cre particles or by the ILV-Cre vectors, were incubated at 37° C./5% CO2 for 14 days. At 14 days post-transduction, the expression of the dsRed is analyzed by flow cytometry. Non-transduced cells (NT) serve for control. This assay is carried out in triplicate. In parallel, HCT116-Lox-dsRed-Lox monoclonal and polyclonal cells were transfected by the pCre plasmid. For this, 50000 HCT116-Lox-dsRed-Lox cells are transfected with 2.6 µg of pCre plasmid using PEI PRO® (Polyplus Transfection).

After extraction of the DNA from the HCT116-Lox-dsRed-Lox cells transduced by the ILV-Cre vectors or by the MS2RLP-Cre particles, or transfected by the pCRE plasmid, the number of copies integrated into the cells is measured by qPCR by detecting a short sequence of the Cre recombinase:

gcatttctggggattgcttataacaccctgttacgtatgccgaaattgccag-gatcagggttaaagatatctca cgtactgacggtgggagaat (SEQ ID No. 2)

with the following pair of qPCR oligonucleotides:

Q-CRE-F: 5'- GCATTTCTGGGGATTGCTTA-3' (SEQ ID No. 3)

Q-CRE-R: 5'- ATTCTCCCACCGTCAGTACG-3'. (SEQ ID No. 4)

II. Results

1. Lentiviral Particle Production Levels

The first assays consisted of comparing the respective production levels of the MS2RLP particles and of the IDLV or ILV vectors. Batches of each type of particle were produced and the titers of the particles were measured by a P24 Elisa test. The results are presented in Table I below:

TABLE 1

Titers of the ILV and IDLV-D64L vectors and of the MS2RLP particles

| Type of particles | Batch No. | Titers of the supernatant PP/mL |
|---|---|---|
| MS2RLP-Luc | rV2.1A1.1740 C2 | $5.5 \times 10^{11}$ |
| IDLV-Luc | rV2.1A1.1732 C2 | $3.1 \times 10^{11}$ |
| ILV-Luc | rV2.1A1.2055 C2 | $6.9 \times 10^{11}$ |

These results show that the three types of particles present equivalent titers (PP/ml+/−) after concentration by the same technique of tangential ultrafiltration. The encapsidation modifications or the mutation of the integrase do not therefore lead to a production deficit of the lentiviral particles.

2. Expression Kinetics in the Target Cells.

A first series of tests was carried out with MS2RLP particles carrying a single type of RNA coding a green fluorescent protein (ZsGreenI) characterized by a long half-life. The results obtained with MS2RLP particles are presented in FIG. VIII and show that the transfer of the RNAs is detected early (as of 8 h post-transduction). The results obtained show a comparable percentage of positive HCT116 cells at 24 hours by the MS2RLP lentiviral particles or the ILV or IDLV-D64L lentiviral vectors. The percentage of positive cells is detectable as of 8 hours for the MS2RLP particles but only as of 24 hours for the ILV and IDLV-D64L vectors. These MS2RLP particles are thus functional and present a capacity equivalent to that of an ILV or of an IDLV-D64L for introducing a coding sequence into a cell population.

In the case of an integrating lentiviral system, the RNAs are retrotranscribed by the RT. The cDNA is then translocated into the nucleus prior to its integration into the host cell genome. It is only as of this step that the transcription then translation of the transgene takes place. In the case of a non-integrating lentiviral system (mutation on the IN), the RNAs are retrotranscribed by the RT. The cDNA is then translocated into the nucleus before being transcribed into RNA then translated as protein.

Only the MS2RLP particles enable an early expression of the transgene on account of the absence of all these intermediate steps. The delivered RNA is directly translated as protein by the cell mechanisms.

A second series of tests was carried out with MS2RLP particles carrying a single type of RNA coding Luciferase (Luc) characterized by a short half-life. The results obtained with MS2RLP particles are present in FIG. IX and show that the optimal activity of the Luciferase is also detected early.

The expression of the Luciferase is transient and it progressively reduces from 8 h to 24 h. By contrast, the expression of fluorescence remains detectable or even stable over this type of kinetic. These results must consider the half-life of the reporter protein used. It is clear that the detection of the reporter gene is proportional to that half-life. The longer it is, the longer the activity related to the protein.

In FIG. X, it is also possible to observe that the luciferase expression intensity varies according to the PP/cell ratio used in the transduction. This dose effect is shown in particular in the Foreskin fibroblasts.

It is thus important to be able to attain high doses of MS2RLP particles to apply to the cells to transduce in order to induce a significant level of expression capable of leading to biological activity. The concentration of the particles appears as a key factor for success. In Foreskin fibroblasts, the expression of Luciferase induced with particles at high dose i.e. 500000 PP/cell, is equivalent to that obtained with conventional integrating lentiviral vectors with a multiplicity of infection (MOI) of 5. The determination of the optimum dose for the transduction of the HCT116 by the MS2RLP particles was carried out under the same conditions as for the Foreskin fibroblasts, by testing doses of 50000, 100000 and 200000 PP/Cell. The dose chosen is 100000 PP/cell, for which the best Luciferase RNA transfer is obtained. The results show that the transduction method must be adapted depending on the permissivity of the target cells.

These results are confirmed by assays of in vivo injection of the MS2RLP-Luc particles which show luciferase expression detection 5 hours after injection.

3. Impact of Production and Purity of the Suspension of MS2RLP Particles on the Transduction Effectiveness.

According to the target cell type, it is important to be able to increase the dose of particles in order to obtain a high number of cells expressing the transported RNAs. It is possible to increase the dose of particles without affecting the viability of the target cells by using purified particles, as shown in application WO 2013/014537. As a matter of act, the final purity of the batch of lentiviral particles is affected by the presence of fetal calf serum (FCS).

To evaluate the impact of the purity of the suspension of MS2RLP particles on Luciferase expression, we compared the Luciferase expression as a function of the purity of two types of supernatant batches:

A supernatant concentrated from MS2RLP particles produced with serum,

A supernatant concentrated from MS2RLP particles produced without serum.

This study was conducted both on HCT116 permissive immortalized cells (FIG. XII) and on primary cells that are less permissive and delicate, Foreskin fibroblasts (FIG. XI).

The results obtained show that the purity of the batch has a high impact on the effectiveness of the transduction of delicate primary cells at high dose. At 500000 PP/cell, the effect of purity is considerable since the activity of the Luciferase is increased by nearly 80% with the batch without serum (FIG. XI). In the presence of FCS, there is by contrast a reduction in luminescence expression.

On very resistant HCT116 immortalized cells, the impact of purity is not detectable on the activity of Luciferase (FIG. XII). By contrast, the batch produced in the presence of serum presents more heterogeneous results, which shows much weaker reproducibility than with the batch produced without serum. This result therefore justifies the choice of producing batches of particles in the absence of serum.

These assays show the necessity of concentrating these lentiviral particles to obtain a high level of expression compatible with induction of a phenotype at cell and tissue level and furthermore shows the impact of the purity of these batches on the effectiveness of gain transfer.

4. Identification of the Optimum Conditions for Gene Transfer by the MS2RLP Particles To increase the effectiveness of RNA transfer, the results obtained by Sutlu et al. (2012) to increase the transduction effectiveness of Natural Killer NK cells were transposed. More particularly, the hypothesis was formulated that the antiviral responses based on the Toll-like receptor (TLR) and/or RIG-I-like receptor (RLR) could restrict the effectiveness of the RNA transfer in certain cells. In order to test this hypothesis, an inhibitor of small signaling molecules TLR and RLR was used during the placing in contact of the cells with the MS2RLP particles. The BX795 molecule is an inhibitor of the BK1/IKKε complex, which acts as a common mediator in the signaling paths of RIG-I, MDA-5, and TLR3.

The use of the BX795 molecule at a concentration of 6 μM considerably increases the transduction effectiveness of HCT116 cells (FIG. XIV) and of Foreskin fibroblasts (FIG. XIII). The observation time (8 h for the MS2RLP particles, 24 h for the ILVs) takes into account the functioning of each particle (FIGS. VIII and IX). A synergistic effect may be observed between the MS2RLP particles and the use of BX795 In the HCT116 cells as in the Foreskin fibroblasts, whereas the BX795 induces a negative effect with the integrating lentiviral vectors ILV in these two cell types. This effect may be linked to a differential in the number of RNA molecules delivered by these two types of particle.

5. Study of Gene Transfer by Luciferase MS2RLP Particles In Vivo.

The injection in vivo of MS2RLP-Luc particles is directed to revealing the expression kinetics of a transgene, in the present case, luciferase, in the various mouse organs injected systemically. A suspension of purified ILV-EF1-Luc Integrating vectors is used as positive control. The measurements are made as of 5 h and up until 7 days post-injection. The intravenous administration engenders a dilution of the injected suspension and therefore a dispersion of the bioluminescence signal which is to be considered. The analyses are therefore made on the whole animal in order to take into account the distribution of the signal throughout the body. A suspension of MS2RLP-Luc particles produced in accordance with the method P1 in the presence of serum and a suspension of MS2RLP-Luc particles purified in accordance with the P2 method are tested. The injection of the suspension of MS2RLP-Luc particles, in accordance with the p2 method in the presence of serum in which the purification is less, led to difficulties both for sampling and for injection. As a matter of fact, this suspension of MS2RLP-Luc particles, obtained by the P1 method in the presence of serum, is characterized by a brown suspension of high viscosity which is particularly difficult to sample with a 29G needle used for in vivo injections. This difficulty arises at the time of delivery of the suspension into the tail vein. The use of a suspension of MS2RLP-Luc particles that was obtained by a P1 method in the presence of serum resulted in poor administration of the particles which become localized in the caudal region of the animal (i.e. at the injection site) and do not pass into the general circulation of the animal (FIG. XV A), times H5 and H8 of the group "MS2RLP-Luc produced in accordance with the P1 method in the presence of serum"). The suspension of MS2RLP-Luc particles obtained by a P1 method in the presence of serum cannot therefore be used in in vivo studies.

Normal administration of the purified suspension of MS2RLP-Luc particles was possible which gives rise to a luciferase expression of 818 ULR at 5 hours after injection. This signal is still visible at 8 hours then disappears at later times (FIGS. XV A, XVI and XVII), "purified MS2RLP-Luc" group) The bioluminescence signal is found mainly in the liver and the spleen (FIG. XV A), "purified MS2RLP-Luc" group). In comparison, at 5 hours, the luminance measured in the animals having received the purified suspension of ILV-EF1-Luc integrating viral vectors is not significant since the reverse transcription and the integration are abortive at these short times. In contrast, at an early stage (5 hours post-injection), the signal obtained with the purified suspension of MS2RLP-Luc particles is significant and attains an expression level twice higher than the signal obtained with the purified suspension of ILV-EF1-Luc integrating viral vectors. After 5 hours, the purified suspension of MS2RLP-Luc particles attains an expression level equivalent to that of the purified suspension of ILV-EF1-Luc integrating viral vectors after 168 h (FIGS. XV B and XVI) group "purified ILV-EF1-Luc". The purified suspension of MS2RLP-Luc particles makes it possible to obtain an optimized transient expression in vivo equivalent to an expression level resulting from an integrating mechanism of lentiviral transduction. The expression is transient on account of the non-integration of the transgene into the genome of the cells. The method of concentration/purification thus makes it possible to obtain suspensions of MS2RLP particles that are effective after in vivo injection.

6. Comparison of the Functionality of the Different Particles

HCT116-Lox-dsRed-Lox cells were generated in advance by transduction with an integrating lentiviral vector bearing the following sequence: EF1-Lox-DsRed-Lox. After obtaining a polyclonal fluorescent line, a monoclonal line was obtained by limiting dilution. It is to be noted that the number of copies of the integrated Lox-DsRed-Lox sequence was quantified by qPCR in polyclonal and monoclonal lines. The number of copies integrated is on average 6 for the polyclonal line and 13 copes for the monoclonal line.

These two lines were transduced by MS2RLP particles carrying the sequence coding for the Cre recombinase enzyme In parallel, these HCT116-Lox-dsRed-Lox cells were transduced by ILV lentiviral vectors carrying the same Cre sequence.

The HCT116-Lox-dsRed-Lox monoclonal and polyclonal cells transduced by the MS2RLP-Cre particles, the ILV-Cre vectors, were incubated at 37° C./5% CO2 for 14 days before cytometer analysis. The results of quantification of the percentage of fluorescent cells by flow cytometry are presented in FIG. XVIII. The results show that the fluorescence has practically disappeared within the polyclonal and monoclonal populations placed in contact with the MS2RLP-Cre particles. As a matter of fact, the percentage of fluorescent cells passed from 100% to less than 10%. The result is much less effective with ILV-Cre integrating vectors (15% reduction) as well as in the condition of transfection of the pCre plasmid (no reduction).

The Integration events after transfer of the nucleic acids coding CRE recombinase in HCT116 cells by MS2RLP-Cre particles, by ILV-Cre vectors, or by pCre plasmids, were verified. To that end, we quantified the number of residual copies of the genome carried by the different types of particles and plasmids, in the HCT116-Lox-dsRed-Lox cells placed in contact with the ILV vectors, the MS2RLP particles or the plasmids coding the CRE protein. To that end, the entirety of the DNAs of the wild-type and modified HCT116 cells was prepared 6 and 14 days after transduction and the DNA coding the CRE recombinase was measured by qPCR.

The results presented in FIG. XIX show that with integrating lentiviral vectors the number of integration events is 4 copies per cell at 6 days. This number is consistent with the multiplicity of infection (MOI) used. The transfection control shows a high number of DNA copies at 6 days, corresponding to the detection of the plasmid present in the cells, then a total disappearance of the copies of Cre DNA at 14 days, on account of the absence of integration of the plasmid into the genome of the target cells.

With the MS2RLP particles, no integration event is detected. As a matter of fact, as the expression is not dependent on the reverse transcriptase or on the LTR ends, these particles deliver the RNA inside target cells which is either directly translated into proteins, or taken by a protein into the nucleus of the cells and does not generate any DNA species.

EXAMPLE 2: TRANSFER OF SEVERAL DIFFERENT RNAS BY SINGLE TRANSDUCTION WITH MS2RLP PARTICLES

I. Equipment and Methods

1. Mono- and Tri-Transduction

This example is conducted using MS2RLP particles or IDLV vectors enabling either the transfer of a single type of RNA enabling the expression of a single protein (ZsGreenI, mCherry or mtBFP), or the transfer of several types of RNA enabling the expression of several different proteins (ZsGreenI+mCherry+mtBFP).

The MS2RLP particles and the non-integrating lentiviral vectors IDLV are produced in the following conditions:
- The particles were produced by transfection of HEK293T cells, with a single expression plasmid coding either ZsGreenI, or mCherry, or mtBFP (as is described in Example 1), in addition to the encapsidation and envelope plasmids,
- The particles are produced by transfection of HEK293T cells with three expression plasmids respectively coding ZsGreenI, mCherry and mtBFP added in equimolar amount, for a total amount of expression plasmids equivalent to the total amount of expression plasmids used for particle production with a single expression plasmid, in addition to the encapsidation and envelope plasmids, The HCT116 particles were transduced by the MS2RLP particles either:
- by transduction with the 3 types of MS2RLP particles ZsGreenI, mCherry or mtBFP independently.
- by mono-transduction with the particles produced with the three expression plasmids coding ZsGreenI, mCherry and mtBFP simultaneously.

In parallel, HCT116 cells are transduced by IDLV vectors either:
- by transduction with the 3 types of IDLV vectors ZsGreenI, mCherry or mtBFP independently.
- by mono-transduction with the IDLV vectors produced with the three expression plasmids coding ZsGreenI, mCherry and mtBFP simultaneously.

The percentage of fluorescent cells was quantified by flow cytometry.

HCT116 cells (ATCC, CCL-247) are seeded in 96-well plates and incubated for 24 h at 37° C./5% CO2. The transduction by MS2RLP particles or the IDLV vectors is carried out in the presence of 4 µg/mL Polybrene. At different times post-transduction (8 h, 24 h and 48 h), the cells are harvested and the percentage of cells expressing the ZsGreenI, the mCherry and the mtBFP is quantified by cytometry (Macs Quant VYB, Miltenyi Biotec). A cell defense mechanism inhibitor, BX795 (InvivoGen), is used at a concentration of 6 µM. Each assay is carried out in triplicate.

II. Results

1. Capacity to Transfer Several Different RNAs in a Single Transduction with MS2RLP Particles The objective of the following assays is to demonstrate the capacity of the MS2RLP particles to transfer several different RNAs into target cells, so making it possible to reduce the number of transductions on the target cells. Thus it becomes possible to transfer several different RNAs in a single transduction rather than to have to perform one transduction per RNA species. For this, we generated three purified batches of MS2RLP particles, under optimum conditions defined in Example 1, that is to say purified batches, produced without serum, according to the method described in application WO 2013/014537. In the production phase of the MS2RLP particles, three types of plasmids coding for fluorescent reporters were used simultaneously in equimolar amounts (ZsGreenI, mCherry and mtBFP), with the encapsidation and envelope plasmids, in order to obtain a batch of MS2RLP particles comprising several different types of RNA. The HCT116 cells were then transduced in the presence of BX795, and the transfer of the different RNAs is observed at 8 h, 24 h and 48 h post-transduction.

FIG. XX illustrates the proportion of tri-fluorescent cells in the green, the red and the blue, after a single transduction of HCT116 cells by MS2RLP particles at two different doses (100000 PP/cell and 300000 PP/cell), or after three simultaneous transductions of MS2RLP particles expressing ZsGreenI or mCherry or mtBFP produced according to Example 1, at a final dose of 300000 PP/cell.

Contrary to the results of Example 1 showing that it is possible to detect the expression of a single fluorescent or luminescent protein at 8 hours, the expression of the three fluorescences at 8 h post-transduction is not detectable, at a dose of 100000 PP/cell. However, 48% of cells are tri-fluorescent at 24 h post-transduction. This proportion of tri-fluorescent cells increases, to attain 60% at 48 h post-transduction. The results thus show that the MS2RLP particles are capable of transporting and transferring at least 3 types of RNA in a single transduction of the target cells.

The determination of the optimum dose of particles per cell is important since it is observed that the increase in the dose of MS2RLP particles leads to a reduction in the number of tri-fluorescent cells (FIG. XX, 300000 PP/cell) in particular 48 hours after transduction. To be precise, if the proportion of tri-fluorescent cells at 300000 PP/cell is a little greater at 8 h post-transduction (5% of tri-fluorescent cells) than at 100000 PP/cell, the proportion of tri-fluorescent cells begins to reduce at 24 h post-transduction by passing from 48% to 40% of tri-fluorescent cells. This difference in transfer effectiveness between the two doses used is all the greater at 48 h post-transduction: as a matter of fact, 43% of tri-fluorescent cells are observed for the dose of 300000 PP/cell as against 60% of tri-fluorescent cells for the dose of 100000 PP/cell.

In parallel, three simultaneous transductions of HCT116 cells with batches of MS2RLP particles produced individually in accordance with example 1 were conducted. The dose used is 100000 PP/cell for each type of fluorescence, i.e. a total dose of 300000 PP/cell. The results show that the percentage of tri-fluorescent cells obtained by three simultaneous transduction of particles carrying only one RNA species is smaller than that induced by a single transduction by particles carrying 3 species of RNA. As a matter of fact, only 7% of tri-fluorescent cells are detected at 8 h post-transduction, then 20% of tri-fluorescent cells at 24 h post-transduction, i.e. only 42% of the level obtained with the single transduction at 100000 PP/cell and 50% of the level obtained with the single transduction at 300000 PP/cell; and lastly 23% of tri-fluorescent cells at 48 h post-transduction, i.e. 38% of the percentage obtained with the single transduction at 100000 PP/cell and 54% of the percentage obtained with the single transduction at 300000 PP/cell. In conclusion, the tri-transduction does not enable percentages of tri-colored cells to be obtained that are as high as those obtained with the three simultaneous transductions.

The revelation of the transfer capacity of different types of RNA in a single transduction of a same batch of MS2RLP particles represents a significant gain over the simultaneous transfer of these different RNAs into target cells. This new property of MS2RLP particles, which directly results in the optimization of the number of transductions to perform, makes it possible not to compromise the viability of the target cells both by too great a number of transductions as well as by the placing of the cells in contact with too great a quantity of particles.

2. Comparison with an IDLV Vector

The same assays as at point 1 above were reproduced with another type of particle in parallel: a viral vector that is Integration-deficient by a mutation in position 64 on the integrase coding sequence (IDLV).

FIG. XXI illustrates the proportion of tri-fluorescent cells in the green, the red and the blue, after a single transduction of HCT116 cells with MS2RLP particles produced with the 3 expression plasmids ZsGreenI, mCherry and mtBFP, in comparison with the three transductions of HCT116 cells with IDLV vectors expressing ZsGreenI or mCherry or mtBFP produced according to Example 1, at a total dose of 300000 PP/cell.

The IDLV vectors are produced in the same conditions as the MS2RLP particles in order to make it possible to perform a single transduction, at the same dose as that used for the MS2RLP particles. At 24 h after the single transduction at a dose of 100000 PP/cell, the proportion of tri-fluorescent cells is slightly greater in the case of the use of IDLV vectors relative to that obtained with the MS2RLP particles (respectively 56% and 48%). This tendency is confirmed at 48 h after the single transduction at a dose of 100000 PP/cell (respectively 80% and 60%).

At 24 h post-transduction, the single transduction of the HCT116 cells by IDLV vectors results in a percentage of tri-colored cells equivalent to that obtained after tri-transduction by IDLV vectors. This tendency remains stable at 48 h post-transduction, with a minimum difference between the 2 transduction methods (71% for the tri-transduction against 81% for the single transduction). Thus, contrary to the results obtained with the MS2RLP particles, the IDLV vectors produced with 3 expression plasmids do not enable a notable increase in the percentage of tri-colored cells at the time of their transduction, in comparison with a tri-transduction. This advantage of the MS2RLP particles is probably explained by their capacity to encapsidate more RNA molecules than the IDLVs or ILVs (which encapsidate strictly 2 molecules only). Thus the expression of 3 different transgenes is facilitated since it does not require the transduction of a same cell by several lentiviral particles.

It will be noted moreover that the percentage of tri-fluorescent cells at 8 h post-transduction is only detectable with the IDLV vectors at 300000 PP/cell in the case of the three transductions or in that of the mono-transduction. By contrast, At 300000 PP/cell, the MS2RLP particles enable tri-fluorescent cells to be detected at 8 h post-transduction (FIG. XX).

In the case of the three mono-transductions by IDLV vectors, the proportion of tri-fluorescent cells is slightly greater at 24 h and 48 h after the three transductions (respectively 60% and 70% of tri-fluorescent cells) than in the case of a single transduction of MS2RLP particles at 100000 PP/cell (respectively 24 h and 48 h of tri-fluorescent cells). It is important to note that this transfer difference is approximately 20% for a dose used for the IDLV vectors 3 times greater than the optimum dose for the MS2RLP particles.

Furthermore, the IDLV particles, although deficient for integration, do not make it possible to avoid residual integrations in the genome of the target cells (Nightingale et al., 2006 and Apolonia et al., 2007). Due to this, the probability of residual integration events increases with the dose of IDLV particles used. The use of MS2RLP particles, by their nature, does not therefore enable this constraint to be avoided by the total absence of residual integration, whatever the integration used.

3. Comparison with an ILV Vector

FIGS. XX and XXII show the transduction profiles for MS2RLP particles and ILV vectors, which are characteristic of the encapsidation of two viral RNA molecules, in conditions making it possible to see a quantitative effect of tri-transduction vs. single transduction (non-saturating conditions).

Transduction of HCT116 Cells by ILV Vectors, Observation at 24 h Post-Transduction (FIG. XXII)

The tri-transduction of the cells with ILV vectors at MOI5 Involving the use of batches of different vectors each coding for a different fluorescent protein (MOI final=3*5=15) makes it possible to obtain 7.5% of cells expressing the three colors. In comparison, the single transduction at the same dose (MOI15) makes it possible to obtain only 0.8% of cells expressing the three colors. As the percentage of cells expressing the three colors thus reduces between tri-transduction and single transduction, the single transduction is not therefore the best adapted method for the use of ILVs. This difference is confirmed at other doses. The tri-transduction of cells with vectors involving the use of batches of different vectors each coding for a different fluorescent protein at MOI20 (MOI final=3*20=60) makes it possible to obtain nearly 75% of cells expressing the three colors while in single transduction at MOI 60, only 38% of cells express the three colors.

Even if the ILV dose used is increased beyond the optimum dose, for example to MOI120, the single transduction of ILV does not make it possible to attain the percentage of cells expressing the three colors obtained in tri-transduction at MOI120 (61.7% vs. 83.3%), nor that obtained in tri-transduction at MOI 60 (61.7% vs. 75.6%).

The MOI 5, 10, 20, 60 used enable operation at non-saturating transduction conditions making it possible to measure actual transductions differences to be measured.

Transduction of HCT116 Cells by MS2RLP Particles. Observation at 24 h Post-Transduction (FIG. XX)

The tri-transduction of cells with MS2RLP particles involving the use of batches of different vectors each coding for a different fluorescent protein at a dose of 10 pg/cell for each batch of MS2RLP particles (final dose=3*10 pg=30 pg/cell) makes it possible to obtain 20% of cells expressing the three colors. As regards the single transduction of cells with MS2RLP particles at the same dose (30 pg/cell), this makes it possible to obtain twice the number of cells expressing the three colors, i.e. 40%. As the percentage of cells expressing the three colors thus doubles between tri-transduction and single transduction, the single transduction is therefore the best adapted method for the use of MS2RLP particles. This result is the opposite of that obtained with ILV vectors.

The MS2RLP particles thus show a different transduction profile to that obtained by the use of ILV vectors which is explained by the difference in the mode of formation of the vectors or particles. As a matter of fact, MS2RLP particles differ from ILV vectors by their heterologous recruitment system for non-viral RNA. In the case of the ILV integrating lentiviral vector, the recruitment by the encapsidation system mediated by the Psi sequence limits the number of RNA viral molecules in the particle to 2. Our results of quantification of the number of RNA molecules in the MS2RLP lentiviral particle estimated that on average, 6 RNA molecules are encapsidated in the MS2RLP particle. These differential encapsidations may explain the differences in transduction by multiple sequences between ILV and MS2RLP.

Furthermore, with the MS2RLP particles in single transduction at 10 pg/cell, which is the optimum use dose, 48% of cells are obtained expressing the three colors, whereas in tri-transduction at a dose 3 times greater (i.e. 30 passage/ cell), only 20% of cells are obtained expressing the three colors, i.e. 2.5 times fewer cells expressing the three colors.

In conclusion, these last results show that only the MS2RLP particles are capable of introducing more than 2 species of RNA into target cells based on a single composition of particles, this being at short times post-transduction or injection (5-8 hours) without inducing an integrating event.

EXAMPLE 3: COMPARISON OF THE TRANSDUCTION EFFECTIVENESS OF HCT116 CELLS BY MS2RLP-ZSGREEN PARTICLES PRODUCED IN ACCORDANCE WITH METHOD P1 OR P2, DESCRIBED IN EXAMPLE 1

I. Equipment and Methods

This example is carried out using MS2RLP particles enabling the transfer of a single type of RNA permitting the expression on a single protein (ZsGreenI).

The particles were produced by transfection of HEK293T cells with a single expression plasmid coding ZsGreenI, (as is described in Example 1), in addition to the encapsidation and envelope plasmids, and by following the production methods P1 or P2, described in Example 1.

HCT116 cells (ATCC, CCL-247) are seeded at 5000 cellules/cm$^2$ in 96-well plates and incubated for 24 h at 37° C./5% CO2.

The transduction by the MS2RLP particles is carried out in the presence of 4 µg/mL Polybrene® with different amounts of MS2RLP particles/cell ((10, 20 and 30 pg p24/cell). At 48 h post-transduction, the cells are harvested and the percentage of cells expressing ZsGreenI as well as the fluorescence intensity are quantified by cytometry (Macs Quant VYB, Miltenyi Biotec). A cell defense inhibitor mechanism, BX795 (InvivoGen), is used at a concentration of 6 µM. Each assay is carried out in triplicate.

II. Results

The objective of this assay is to compare the effectiveness of the transduction of HCT116 cells by MS2RLP-ZsGreen particles produced in accordance with the method P1 or P2. The results presented in FIG. XXIII show that the RNA transfer capacity is not impacted by the production method since the percentage of transduced cells is the same whatever the production method used. However, only the expression of the transgene is impacted by the production method. As a matter of fact, the purified particles make it possible to obtain the highest expression level of the protein of interest, whatever the dose of MS2RLP particles used.

EXAMPLE 4: CONSTRUCTION OF MS2RLP LENTIVIRAL PARTICLES BY MODIFYING THE NUCLEOCAPSID AND TEST FOR THE NUMBER OF REPETITIONS OF THE STEM-LOON MOTIF OF THE MS2 RNA

I. Equipment and Methods
1. Plasmid Construction
Expression plasmid for a sequence of interest: The expression plasmid bears a promoter-sequence of interest-polyA expression cassette (see FIG. II) with or without an RNA stabilizing or intronic sequence. In order to transport the mRNAs into the lentiviral particles, several repetitions of the stem-loop motif of the MS2 RNA (ctagaaaacatgaggatcacccatgtctgcag, SEQ ID No. 1) were inserted inside an expression cassette downstream of the reporter gene:

2 repetitions (FIG. XXIV)
6 repetitions (FIG. XXV)
12 repetitions (FIG. XXVI

The sequence of interest chosen is that of native Firefly Luciferas.

Encapsidation plasmid: the encapsidation plasmid is that described in Example 1 (FIG. IIIb).
Envelope plasmid (pENV): the encapsidation plasmid is that described in Example 1 (FIG. IV).

2. Production, Concentration/Purification and Titration of the Lentiviral Particles The lentiviral particles are produced as described in Example 1 and are concentrated and purified according to method P1 as described in Example 1.

3. Expression Kinetics for Luciferase

HCT116 cells (ATCC, CCL-247) are seeded in 96-well plates and incubated for 24 h at 37° C./5% CO2. The transduction by the MS2RLP2X, 6X, 12X particles is carried out at a dose of 100 000 PP/cell (10 pg p24/cell), in the presence of 4 µg/mL Polybrene®. The transduction supernatant is eliminated 4 hours after and replaced by fresh supplemented growth medium. At 4 h, 8 h, 24 h, 32 h, and 48 h post-transduction, the cells are harvested and the expression of the Luciferase is analyzed using the kit OneGlo Luciferase assay (Promega) following the recommendations of the supplier and using the Synergy H1 Hybrid microplate reader (Biotek). Each test is carried out in triplicate. The control is carried out by non-transduced HCT116 cells.

II. Results

The results are presented in FIG. XXVII. The objective of this assay is to verify that it is possible to reduce the number of repeated motifs of the MS2 sequence on the expression plasmid without the expression level of the RNA to deliver being impacted. The expression kinetics of the Luciferase presents an increase in the luminescence signal from 4 h to 8 h showing that in the case of a protein with a short life, the maximum expression is attained early, whatever the number of motifs of the MS2 sequence that are repeated. After 8 h, the activity of the Luciferase reduces, until at 48 h it attains the same level as at 4 h post-transduction (between 10 000 and 20 000 URL). The construction bearing 2 and 6 repeated motifs of the MS2 sequence show the same Luciferase expression profile over time. However, the expression of Luciferase by the construction bearing 12 repeated motifs of the MS2 sequence is 30% higher than the constructions bearing 2 or 6 repeated motifs. Therefore, the MS2RLP particles are effective for delivering RNAs whatever the number of repeated motifs used. According to the application, the number of repetitions of the MS2 motif will have to be adapted.

EXAMPLE 5: CONSTRUCTION OF MS2RLP LENTIVIRAL PARTICLES BY MODIFYING THE LUCIFERASE AND TEST FOR THE NUMBER OF REPETITIONS OF THE STEM-LOOP MOTIF OF THE MS2 RNA

I. Equipment and Methods
1. Plasmid Construction
Expression plasmid for a sequence of interest: The expression plasmid bears a promoter-sequence of interest-polyA expression cassette (see FIG. II) with or without an RNA stabilizing or intronic sequence. In order to transport the mRNAs into the lentiviral particles, several repetitions of the stem-loop motif of the MS2 RNA (ctagaaaacatgaggatcacccatgtctgcag, SEQ ID No. 1) were inserted inside an expression cassette downstream of the reporter gene:

2 repetitions (FIG. XXIV)
6 repetitions (FIG. XXV)
12 repetitions (FIG. XXVI

The promoter used may be that of CMV (FIG. IIa) or EF1 (FIGS. IIb) but other promoters may be used. The sequence of interest may be a DNA coding a reporter protein such as native Firefly Luciferase (FIG. IIa), a green (ZsGreenI), red (mCherry) or blue (mtBFP) fluorescent protein (FIG. IIb), or a cDNA coding a protein, for example the CRE protein (FIG. IIc). The sequence of interest may also be that of an shRNA, an miRNA, an sgRNA, an LncRNA or of an circRNA.

Encapsidation plasmid: The lentiviral particle was modified to contain within the integrase, the sequence of the Coat protein of the bacteriophage MS2. The p8.74 encapsidation plasmid (FIG. VI), carrier of the genes coding the structural and functional proteins (Gag, Pol), used for the production of the MS2RLP particles is modified according to the strategy illustrated by FIG. I: this p8.74 plasmid is used to generate, by PCR assembly, a plasmid on which the Coat protein of the phage MS2 is merged with the C-terminal domain of the integrase. This merging, obtained by HpaI cloning, makes it possible to generate the Linear Coat p8.74-POL-MS2 plasmid (FIG. XXVIII). A construction is thus obtained as illustrated in FIG. I (p8.74.IN-coat). The Pol coding sequence may be deleted or mutated in certain functional elements for example such as the sequence coding reverse transcriptase (RT).

Envelope plasmid (pENV): This plasmid carries the gene coding an envelope protein, which may be the VSVG coding the envelope protein of the Vesicular stomatitis virus (FIG. IV).

2. Production, Concentration/Purification and Titration of the Lentiviral Particles The lentiviral particles are produced as described in Example 1, in accordance with the P1 method.

3. Expression Kinetics for Luciferase

HCT116 cells (ATCC, CCL-247) are seeded in 96-well plates and incubated for 24 h at 37° C./5% CO2. The transduction by the MS2(IN)-RLP2X, 6X, 12X particles produced in accordance with the P1 method is carried out at a dose of 5 pg p24/cell, in the presence of 8 μg/mL Polybrene®. The transduction supernatant is eliminated 4 hours after and replaced by fresh supplemented growth medium. At 4 h, 8 h, 24 h, 32 h, and 48 h post-transduction, the cells are harvested and the expression of the Luciferase is analyzed using the kit OneGlo Luciferase assay (Promega) following the recommendations of the supplier and using the Synergy H1 Hybrid microplate reader (Biotek). This test is carried out in triplicate. The control is carried out by non-transduced HCT116 cells.

II. Results

The results are presented in FIG. XXIX. The objective of this assay is to verify that it is possible transfer RNAs into the lentiviral particles with MS2-Coat into the integrase and reduce the number of repeated motifs of the MS2 sequence on the expression plasmid without the expression level of the RNA to deliver being impacted. The maximum expression of Luciferase is attained early, whatever the number of repeated motifs of the MS2 sequence. The strongest luminescence signal of the Luciferase expression kinetics is obtained as of 4 h and until 24 h. After 24 h, the Luciferase activity reduces until it attains a signal 2 to 4 times weaker than for the conditions at 4/8/24 h. The MS2(IN)-RLP particles thus make it possible to deliver RNAs, whatever the number of repeated motifs of the MS2 sequence.

EXAMPLE 6: CONSTRUCTION OF PP7(NC)-RLP LENTIVIRAL PARTICLES AND TEST FOR THE DOSE EFFECT OF THE PP7RLP PARTICLES ON THE TRANSDUCTION OF HCT116 CELLS

I. Equipment and Methods
1. Plasmid Construction
1.1 Plasmids for the Production of PP7(NC)-RLP Luc 12X Lentiviral Particles Expression plasmid for a sequence of interest: The expression plasmid bears a promoter-sequence of interest-polyA expression cassette (see FIG. XXX) with or without an RNA stabilizing or intronic sequence. In order to transport the mRNAs into the lentiviral particles, 12 repetitions of the stem-loop motif of the PP7 RNA (ctagaaggagcagacgatatggcgtcgctccctgcag SEQ ID No. 5) were inserted inside an expression cassette downstream of the reporter gene.

The promoter used may be that of CMV or EF1 (FIG. XXX) but other promoters may be used. The sequence of interest may be a DNA coding a reporter protein such as native Firefly Luciferase (FIG. IIa), a green (ZsGreenI), red (mCherry) or blue (mtBFP) fluorescent protein (FIG. IIb), or a cDNA coding a protein, for example the CRE protein (FIG. IIc). The sequence of interest may also be that of an shRNA, an miRNA, an sgRNA, an LncRNA or of an circRNA.

Encapsidation plasmid: The lentiviral particle was modified to contain the Coat protein sequence of the bacteriophage PP7 within the nucleocapsid protein, instead of and in place of the second Zn finger domain The p8.74 encapsidation plasmid, carrier of the genes coding the structural and functional proteins (Gag, Pol), used for the production of the PP7RLP particles is modified according to the strategy illustrated by FIG. XXXI: this p8.74 plasmid is used to generate, by PCR assembly, a plasmid lacking the second zinc finger of the p8.74ΔZF nucleocapsid protein. The second zinc finger is substituted by the Coat protein of the phage PP7 by HpaI cloning, to generate the p8.74ΔZF-PP7-Coat plasmid. The construction illustrated in FIG. XXXII is thereby obtained. The sequence coding Pol may be deleted or mutated in some functional elements for example such as the sequence coding the reverse transcriptase (RT) or the integrase (IN) without altering the function of the PP7RLPs.

Envelope plasmid (pENV): This plasmid carries the gene coding an envelope protein, which may be the VSVG coding the envelope protein of the Vesicular stomatitis virus (FIG. IV).

1.2 Plasmids for the Production of MS2(NC)-RLP Luc 12X Lentiviral Particles

The plasmids used are identical to those used in Example 1.

2. Production, Concentration/Purification and Titration of the Lentiviral Particles The lentiviral particles are produced as described in Example 1, in accordance with the P1 method.

3. Dose Effect of the PP7(NC)-RLP-Luc Particles

HCT116 cells (ATCC, CCL-247) are seeded in 96-well plates and incubated for 24 h at 37° C./5% CO2. The transduction by the PP7(NC)-RLP-Luc-12X particles, produced in accordance with the P1 method is carried out at a dose ranging from 0 to 20 pg p24/cell, in the presence of 8

µg/mL Polybrene®. At 4 h post-transduction, the cells are harvested and the expression of the Luciferase is analyzed using the kit OneGlo Luciferase assay (Promega) following the recommendations of the supplier and using the Synergy H1 Hybrid microplate reader (Biotek). This test is carried out in triplicate. The control is carried out by non-transduced HCT116 cells.

II. Results

The results are presented in FIG. XXXIII. The objective of this assay is, in a first phase, to see whether the RNA/protein interaction system of the PP7 bacteriophage enables RNA encapsidation on forming RLP particles. In a second phase, this assay makes it possible to determine the best experimental conditions of use for the PP7(NC)-RLP particles.

FIG. XXXIII shows that as of the dose of 1 pg p24/cell, the Luciferase activity is strongly detected. The more the dose of PP7(NC)-RLP is increased, the higher the Luciferase activity. Furthermore, in comparison with the MS2(NC)-RLP vector used at the same dose as the PP7(NC)-RLP, the Luciferase activity signal is very highly comparable.

This assay shows that with 12 repeated motifs of the PP7 sequence, the RNA encapsidation system by the Coat protein of the PP7 bacteriophage operates equally well as the system resulting from the bacteriophage MS2, and that to obtain a very high expression of the protein of interest, a dose of 10 µg p24/cell may be adopted.

EXAMPLE 7: CONSTRUCTION OF PP7(NC)-RLP LENTIVIRAL ARTICLES AND TEST OF THE NUMBER OF REPETITIONS OF THE STEM-LOOP MOTIF OF THE PP7 RNA

I. Equipment and Methods

1. Plasmid Construction 1.1 Plasmids for the Production of PP7(NC)-RLP Lentiviral Particles Expression plasmid for a sequence of interest: The expression plasmid bears a promoter-sequence of interest-polyA expression cassette (see FIG. XXX) with or without an RNA stabilizing or intronic sequence. In order to transport the mRNAs into the lentiviral particles, several repetitions of the stem-loop motif of the PP7 RNA (ctagaaggagcagacgatatggcgtcgctccctgcag SEQ ID No. 5) were inserted inside an expression cassette downstream of the reporter gene.

2 repetitions (FIG. XXXIVa)
6 repetitions (FIG. XXXV)
12 repetitions (FIG. XXX)

The promoter used may be that of CMV or EF1 (FIG. XXX) but other promoters may be used. The sequence of interest may be a DNA coding a reporter protein such as native Firefly Luciferase (FIG. XXXIVa), a green (Zs-GreenI), red (mCherry) or blue (mtBFP) fluorescent protein (FIG. XXXIVb), or a cDNA coding a protein, for example the CRE protein. The sequence of interest may also be that of an shRNA, an miRNA, an sgRNA, an LncRNA or of an circRNA.

Encapsidation plasmid: The lentiviral particle was modified to contain the Coat protein sequence of the bacteriophage PP7 within the nucleocapsid protein, instead of and in place of the second Zn finger domain The p8.74 encapsidation plasmid, carrier of the genes coding the structural and functional proteins (Gag, Pol), used for the production of the PP7RLP particles is modified according to the strategy illustrated by FIG. XXXI: this p8.74 plasmid is used to generate, by PCR assembly, a plasmid lacking the second zinc finger of the p8.74ΔZF nucleocapsid protein. The second zinc finger is substituted by the Coat protein of the phage PP7 by HpaI cloning, to generate the p8.74ΔZF-PP7-Coat plasmid. The construction illustrated in FIG. XXXII is thereby obtained. The sequence coding Pol may be deleted or mutated in some functional elements for example such as the sequence coding the reverse transcriptase (RT) or the integrase (IN) without altering the function of the PP7RLPs.

Envelope plasmid (pENV): This plasmid carries the gene coding an envelope protein, which may be the VSVG coding the envelope protein of the Vesicular stomatitis virus (FIG. IV).

1.2 Plasmids for the Production of MS2(NC)-RLP Luc 12X Lentiviral Particles

The plasmids used are identical to those used in Example 1.

2. Production, Concentration/Purification and Titration of the Lentiviral Particles The lentiviral particles are produced as described in Example 1, in accordance with the P1 method.

3. Expression Kinetics for Luciferase

HCT116 cells (ATCC, CCL-247) are seeded in 96-well plates and incubated for 24 h at 37° C./5% CO2. The transduction by the PP7(NC)-RLP-Luc-2X, 6X, 12X particles produced in accordance with the P1 method is carried out at a dose of 10 pg p24/cell, in the presence of 8 µg/mL Polybrene®. The transduction supernatant is eliminated 4 hours after and replaced by fresh supplemented growth medium. At 4 h, 8 h, 24 h, 32 h, and 48 h post-transduction, the cells are harvested and the expression of the Luciferase is analyzed using the kit OneGlo Luciferase assay (Promega) following the recommendations of the supplier and using the Synergy H1 Hybrid microplate reader (Biotek). This test is carried out in triplicate. The control is carried out by non-transduced HCT116 cells.

II. Results

The results are presented in FIG. XXXVI. The objective of this assay is to show the impact of the modifications of the number of repeated motifs of the PP7 sequence on the encapsidation capacity and thus on the transfer of RNA into target cells, at several given times. The PP7(NC)-RLP particles comprising the PP7 motif repeated 2 times, 6 times or 12 times enabling the transfer of RNA in proportions comparable to those obtained with MS2(NC)-RLP particles comprising the MS2 motif 12 times. The PP7(NC)-RLP particles are thus effective for delivering RNAs whatever the number of repeated motifs used. According to the type of application the number of repetitions could therefore be adapted. The results show that, in the conditions of the assay, the PP7(NC)-RLP particles comprising the PP7 motif repeated 2 times or 6 times enable more effective transfer of RNA than that obtained by the use of MS2(NC)-RLP particles comprising the MS2 motif 12 times. The expression kinetics of the Luciferase presents an increase in the luminescence signal from 4 h to 8 h, showing that in the case of a protein with a short life, the maximum expression is attained early, whatever the number of motifs of the PP7 sequence that are repeated. After 24 h, the Luciferase activity diminishes, until at 32 h and 48 h it attains a luminescence signal 4 to 5 less intense than for the condition 8 h post-transduction.

EXAMPLE 8: CONSTRUCTION OF PP7(IN)-RLP LENTIVIRAL PARTICLES BY MODIFYING THE INTEGRASE AND TEST FOR THE NUMBER OF REPETITIONS OF THE STEM-LOOP MOTIF OF THE PP7 RNA

I. Equipment and Methods

1. Plasmid Construction

Expression plasmid for a sequence of interest: The expression plasmid bears a promoter-sequence of interest-polyA expression cassette (see FIG. XXX) with or without an RNA stabilizing or intronic sequence. In order to transport the mRNAs into the lentiviral particles, several repetitions of the stem-loop motif of the PP7 RNA (ctagaaggagcagacgatatggcgtcgctccctgcag SEQ ID No. 5) were inserted inside an expression cassette downstream of the reporter gene.

2 repetitions (FIG. XXXIVa)
6 repetitions (FIG. XXXV)
12 repetitions (FIG. XXX)

The promoter used may be that of CMV or EF1 (FIG. XXX) but other promoters may be used. The sequence of interest may be a DNA coding a reporter protein such as native Firefly Luciferase (FIG. XXXIVa), a green (ZsGreenI), red (mCherry) or blue (mtBFP) fluorescent protein (FIG. XXXIVb), or a cDNA coding a protein, for example the CRE protein (FIG. XXXIVc). The sequence of interest may also be that of an shRNA, an miRNA, an sgRNA, an LncRNA or of an circRNA.

Encapsidation plasmid: The lentiviral particle was modified to contain within the integrase, the sequence of the Coat protein of the bacteriophage PP7. The p8.74 encapsidation plasmid, carrier of the genes coding the structural and functional proteins (Gag, Pol), used for the production of the PP7(IN)-RLP particles is modified according to the strategy illustrated by FIG. XXXVII: this p8.74 plasmid is used to generate, by PCR assembly, a plasmid on which the Coat protein of the phage PP7 is merged with the C-terminal domain of the integrase. This merging, obtained by HpaI cloning, makes it possible to generate the Coat p8.74-POL-MS2 plasmid. The construction illustrated in FIG. XXXVIII is thereby obtained. The Pol coding sequence may be deleted or mutated in certain functional elements for example such as the sequence coding reverse transcriptase (RT).

Envelope plasmid (pENV): This plasmid carries the gene coding an envelope protein, which may be the VSVG coding the envelope protein of the Vesicular stomatitis virus (FIG. IV).

2. Production, Concentration/Purification and Titration of the Lentiviral Particles The lentiviral particles are produced as described in Example 1, in accordance with the P1 method.

3. Expression Kinetics for Luciferase

HCT116 cells (ATCC, CCL-247) are seeded in 96-well plates and incubated for 24 h at 37° C./5% CO2. The transduction by the PP7(IN)-RLP-Luc-2X, 6X, 12X particles produced in accordance with the P1 method is carried out at a dose of 2.8 pg p24/cell, in the presence of 8 µg/mL Polybrene®. The transduction supernatant is eliminated 4 hours after and replaced by fresh supplemented growth medium. At 4 h, 8 h, 24 h, 32 h, and 48 h post-transduction, the cells are harvested and the expression of the Luciferase is analyzed using the kit OneGlo Luciferase assay (Promega) following the recommendations of the supplier and using the Synergy H1 Hybrid microplate reader (Biotek).

This test is carried out in triplicate. The control is carried out by non-transduced HCT116 cells.

II. Results

The results are presented in FIG. XXXIX. The objective of this assay is to verify that it is possible to transport RNAs into the lentiviral particles with PP7-Coat in the integrase and to show the impact of the modifications of the number of repeated motifs of the PP7 sequence on the encapsidation capacity and thus on the transfer of RNA into target cells at several given times. The maximum expression of Luciferase is attained at 8 h, whatever the number of repeated motifs of the PP7 sequence. After 8 h the Luciferase activity diminishes, whatever the number of repeated motifs of the PP7 sequence, and the difference in Luciferase activity between the different numbers of repeated motifs is not statistically significant. The PP7(IN)-RLP particles therefore enable RNAs to be delivered.

EXAMPLE 9: TRANSFER OF SEVERAL DIFFERENT RNAS BY SINGLE TRANSDUCTION WITH PP7RLP PARTICLES

I. Equipment and Methods

1. Mono- and Tri-Transduction

This example is conducted using PP7RLP particles or ILV vectors enabling either the transfer of a single type of RNA enabling the expression of a single protein (ZsGreenI, mCherry or mtBFP), or the transfer of several types of RNA enabling the expression of several different proteins (ZsGreenI+mCherry+mtBFP).

The PP7RLP particles and the integrating lentiviral vectors ILV are produced in the following conditions:

The particles were produced by transfection of HEK293T cells, with a single expression plasmid coding either ZsGreenI, or mCherry, or mtBFP (as is described in Example 1), in addition to the encapsidation and envelope plasmids, The particles are produced by transfection of HEK293T cells with three expression plasmids respectively coding ZsGreenI, mCherry and mtBFP added in equimolar amount, for a total amount of expression plasmids equivalent to the total amount of expression plasmids used for particle production with a single expression plasmid, in addition to the encapsidation and envelope plasmids.

The HCT116 particles were transduced by the PP7RLP particles either by transduction with 3 types of PP7RLP particles, ZsGreenI, mCherry or mtBFP independently, or by co-transduction of the 3 types of PP7RLP particles at the same time.

by mono-transduction with the particles produced with the three expression plasmids coding ZsGreenI, mCherry and mtBFP simultaneously.

In parallel, HCT116 cells are transduced by ILV vectors either:

by transduction with 3 types of ILV vectors, ZsGreenI, mCherry or mtBFP independently, or by co-transduction of the 3 types of ILV particles at the same time.

by mono-transduction with the ILV vectors produced with the three expression plasmids coding ZsGreenI, mCherry and mtBFP simultaneously.

The percentage of fluorescent cells was quantified by flow cytometry.

HCT116 cells (ATCC, CCL-247) are seeded in 24-well plates and incubated for 24 h at 37° C./5% CO2. The transduction by PP7RLP particles or the ILV vectors is carried out in the presence of 8 μg/mL Polybrene. At 24 h post-transduction, the cells are harvested and the percentage of cells expressing the ZsGreenI, the mCherry and the mtBFP is quantified by cytometry (Macs Quant VYB, Miltenyi Biotec). A cell defense inhibitor mechanism, BX795 (InvivoGen), is used at a concentration of 6 μM. Each assay is carried out in triplicate.

II. Results

1. Capacity to Transfer Several Different RNAs in a Single Transduction with PP7RLP Particles in Comparison with ILV The objective of the following assays is to demonstrate the capacity of the PP7RLP particles to transfer several different RNAs into target cells, so making it possible to reduce the number of transductions on the target cells. Thus it becomes possible to transfer several different RNAs in a single transduction rather than to have to perform one transduction per RNA species. For this, purified batches of PP7RLP particles were generated under optimum conditions defined in Example 1, that is to say purified batches, produced without serum, according to method P1 of Example 1 described in application WO 2013/014537. In the production phase of the PP7RLP particles, three types of plasmids coding for fluorescent reporters were used simultaneously in equimolar amounts (ZsGreenI, mCherry and mtBFP), with the encapsidation and envelope plasmids, in order to obtain a batch of PP7RLP particles comprising several different types of RNA. The HCT116 cells were then transduced in the presence of BX795, and the transfer of the different RNAs is observed at 24 h post-transduction.

FIG. XL illustrates the proportion of tri-fluorescent cells in the green, the red and the blue, after a single transduction of HCT116 cells by PP7RLP particles at two different doses (10 pg p24/cell and 30 pg p24/cell), or after three simultaneous transductions of PP7RLP particles expressing ZsGreenI or mCherry or mtBFP produced according to Example 1, at a final dose of 30 pg p24/cell.

88% of the cells are tri-fluorescent when they are transduced at a dose of 30 pg p24/cell with the PP7RLP batch containing particles carrying the 3 RNA species, whereas only 1% of the cells are fluorescent when they are transduced by the batch of ILV vectors obtained by co-transfection of the 3 batch each containing a different fluorescent protein.

The results thus show that the PP7RLP particles are capable of transporting and transferring at least 3 types of RNA in a single transduction of the target cells. These particles enable the transfer of multiple RNAs much more effectively than with the ILV vector.

The transduction of cells by multiple RNAs is thus much more effective and simpler with the PP7RLP particles than with ILV, for a result that is greater by at least 70%.

91% of the cells are tri-fluorescent when they are transduced simultaneously at a total dose of 30 pg p24/cell with the 3 separate batches of PP7RLP each containing a single RNA species. The comparison of the effectiveness of the simultaneous expression of several transgenes in mono-transduction or multi-transductions shows an equivalent effectiveness for the PP7RLP vector (88% vs 91% respectively).

This effectiveness thus makes it possible to reduce the multiplicity of infection relative to the use of batches of particles produced independently. The risk of cell toxicity is considerably reduced thereby. This makes it possible not to compromise the viability of the target cells both by too great a number of transductions and by placing the cells in contact with too high a quantity of particles.

---

The invention claimed is:

1. A retroviral particle comprising a protein from a Gag polyprotein, an envelope protein, optionally an integrase, and at least two encapsidated, different, non-viral RNAs, the at least two encapsidated, different, non-viral RNAs each comprising an RNA sequence of interest linked to an encapsidation sequence, each encapsidation sequence bound to a heterologous binding domain introduced into the protein from the Gag polyprotein.

2. The retroviral particle according to claim 1, wherein the protein from the Gag polyprotein is a nucleocapsid protein.

3. The retroviral particle according to claim 2, which is a lentiviral particle.

4. The retroviral particle which is a lentiviral particle according to claim 3, wherein:
   the binding domain is the Coat protein of bacteriophage MS2;
   each of the encapsidation sequences of the non-viral RNAs is a stem-loop sequence of MS2; and
   the nucleocapsid protein is the nucleocapsid protein (NC) of HIV, wherein the Coat protein is inserted at the second zinc finger of the NC.

5. The retroviral particle which is a lentiviral particle according to claim 3, wherein:
   the binding domain is the Coat protein of bacteriophage PP7;
   each of the encapsidation sequences of the non-viral RNAs is a stem-loop sequence of PP7; and
   the nucleocapsid protein is the nucleocapsid protein (NC) of HIV, wherein the Coat protein is inserted at the second zinc finger of the NC.

6. A composition comprising a plurality of the retroviral particle according to claim 1.

* * * * *

SEQUENCE LISTING

```
<160> NUMBER OF SEQ ID NOS: 5

<210> SEQ ID NO 1
<211> LENGTH: 32
<212> TYPE: DNA
<213> ORGANISM: Artificial Sequence
<220> FEATURE:
<223> OTHER INFORMATION: stem-loop sequence of bacteriophage MS2
<220> FEATURE:
<221> NAME/KEY: misc_feature
<223> OTHER INFORMATION: Synthetic

<400> SEQUENCE: 1
ctagaaaaca tgaggatcac ccatgtctgc ag                                32

<210> SEQ ID NO 2
<211> LENGTH: 95
<212> TYPE: DNA
<213> ORGANISM: Artificial Sequence
<220> FEATURE:
<223> OTHER INFORMATION: short sequence of Cre recombinase
<220> FEATURE:
<221> NAME/KEY: misc_feature
<223> OTHER INFORMATION: Synthetic

<400> SEQUENCE: 2
gcatttctgg ggattgctta taacaccctg ttacgtatag ccgaaattgc caggatcagg    60
gttaaagata tctcacgtac tgacggtggg agaat                              95

<210> SEQ ID NO 3
```

```
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<223> OTHER INFORMATION: Synthetic

<400> SEQUENCE: 3
gcatttctgg ggattgctta                                               20

<210> SEQ ID NO 4
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<223> OTHER INFORMATION: Synthetic

<400> SEQUENCE: 4
attctcccac cgtcagtacg                                               20

<210> SEQ ID NO 5
<211> LENGTH: 37
<212> TYPE: DNA
<213> ORGANISM: Artificial Sequence
<220> FEATURE:
<223> OTHER INFORMATION: stem-loop sequence of phage PP7
<220> FEATURE:
<221> NAME/KEY: misc_feature
<223> OTHER INFORMATION: Synthetic

<400> SEQUENCE: 5
ctagaaggag cagacgatat ggcgtcgctc cctgcag                            37
```